United States Patent
Dombrowski et al.

(10) Patent No.: US 7,553,972 B2
(45) Date of Patent: Jun. 30, 2009

(54) BENZAMIDE INHIBITORS OF THE P2X$_7$ RECEPTOR

(75) Inventors: Mark A. Dombrowski, Waterford, CT (US); Allen J. Duplantier, Ledyard, CT (US); Chakrapani Subramanyam, South Glastonbury, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 11/673,246

(22) Filed: Feb. 9, 2007

(65) Prior Publication Data

US 2007/0142329 A1 Jun. 21, 2007

Related U.S. Application Data

(63) Continuation of application No. 10/844,251, filed on May 12, 2004, now Pat. No. 7,186,742.

(60) Provisional application No. 60/470,001, filed on May 12, 2003.

(51) Int. Cl.
*C07D 211/70* (2006.01)
*C07D 241/02* (2006.01)
*C07D 237/00* (2006.01)
(52) U.S. Cl. .................. 546/348; 544/408; 544/239
(58) Field of Classification Search .................. 546/348; 544/239, 408
See application file for complete search history.

(56) References Cited

U.S. PATENT DOCUMENTS

| | | | |
|---|---|---|---|
| 5,077,409 A | 12/1991 | Wissner | |
| 5,128,351 A | 7/1992 | Wissner | |
| 5,281,571 A | 1/1994 | Woodard et al. | |
| 5,686,061 A | 11/1997 | Li | |
| 5,773,646 A | 6/1998 | Chandrakumar | |
| 5,939,418 A | 8/1999 | Quan et al. | |
| 5,961,376 A | 10/1999 | Gottschald | |
| 6,001,862 A | 12/1999 | Maeda | |
| 6,030,990 A | 2/2000 | Maeda | |
| 6,147,101 A | 11/2000 | Maeda | |
| 6,180,844 B1 | 1/2001 | Fujita | |
| 6,187,797 B1 | 2/2001 | Pruitt et al. | |
| 6,201,024 B1 | 3/2001 | Baxter et al. | |
| 6,201,130 B1 | 3/2001 | Schwab et al. | |
| 6,242,470 B1 | 6/2001 | Baxter et al. | |
| 6,258,838 B1 | 7/2001 | Baxter et al. | |
| 6,265,409 B1 | 7/2001 | Cheshire et al. | |
| 6,297,239 B1 | 10/2001 | deSolms et al. | |
| 6,303,659 B2 | 10/2001 | Baxter et al. | |
| 6,320,078 B1 | 11/2001 | Suzuki et al. | |
| 6,335,333 B1 | 1/2002 | Schwab et al. | |
| 6,451,824 B1 | 9/2002 | Thorwart et al. | |
| 6,492,355 B1 | 12/2002 | Alcaraz et al. | |
| 6,653,312 B1 | 11/2003 | Auvin et al. | |
| 6,720,452 B2 | 4/2004 | Alcaraz et al. | |
| 6,927,219 B2 | 8/2005 | Duplantie | |
| 6,974,812 B2 | 12/2005 | Dombrowski et al. | |
| 7,176,202 B2 | 2/2007 | Dombrowski et al. | |
| 2001/0003121 A1 | 6/2001 | Baxter et al. | |
| 2002/0193414 A1 | 12/2002 | Alcaraz et al. | |
| 2003/0013704 A1 | 1/2003 | Alcaraz et al. | |
| 2003/0013721 A1 | 1/2003 | Meghani et al. | |
| 2003/0032807 A1 | 2/2003 | Andree et al. | |
| 2003/0040513 A1 | 2/2003 | Baxter et al. | |
| 2003/0087945 A1 | 5/2003 | Thorwart et al. | |
| 2003/0144293 A1 | 7/2003 | Duplantier | |
| 2003/0149692 A1 | 8/2003 | Mitchell | |
| 2003/0186981 A1 | 10/2003 | Duplantier et al. | |
| 2005/0009900 A1 | 1/2005 | Dombrowski et al. | |
| 2005/0288256 A1 | 12/2005 | Li | |
| 2005/0288288 A1 | 12/2005 | Leonard et al. | |
| 2006/0018904 A1 | 1/2006 | Chung et al. | |
| 2006/0040939 A1 | 2/2006 | Dombroski et al. | |
| 2006/0058302 A1 | 3/2006 | Duplantier et al. | |
| 2006/0211709 A1 * | 9/2006 | Buhr et al. ............. 514/255.05 |

FOREIGN PATENT DOCUMENTS

| | | |
|---|---|---|
| EP | 0138527 A2 | 4/1985 |
| EP | 0881219 B1 | 7/2004 |
| WO | WO-92/11242 | 7/1992 |
| WO | WO-93/04686 | 3/1993 |
| WO | WO-98/43973 | 10/1998 |
| WO | WO-99/29686 | 6/1999 |
| WO | WO-00/35864 | 6/2000 |
| WO | WO-00/71509 A1 | 11/2000 |
| WO | WO 02/094767 A2 | 11/2002 |
| WO | WO 03/042191 A1 | 5/2003 |
| WO | WO-2004/058270 A1 | 7/2004 |
| WO | WO-2004/058731 A1 | 7/2004 |
| WO | WO 2004/099146 A1 | 11/2004 |
| WO | WO 2006/003500 A1 | 1/2006 |
| WO | WO 2006/003517 A1 | 1/2006 |

OTHER PUBLICATIONS

Drug Development Research (1996), 37(3), p. 126.

(Continued)

*Primary Examiner*—Rebecca L Anderson
*Assistant Examiner*—Robert Havlin
(74) *Attorney, Agent, or Firm*—Julie M. Lappin

(57) ABSTRACT

The present invention provides benzamide inhibitors of the P2X$_7$ receptor of the formula:

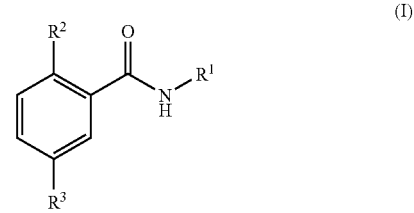

(I)

wherein $R^1$-$R^3$ are as defined herein. The compounds of the invention are useful in the treatment of IL-1 mediated disorders, including, without limitation, inflammatory diseases such as osteoarthritis and rheumatoid arthritis; allergies, asthma, COPD, cancer, reperfusion or ischemia in stroke or heart attack, autoimmune diseases and other disorders.

3 Claims, No Drawings

OTHER PUBLICATIONS

Aranapakam, et al., "5-fluoro-2-methyl-N-[5-(5H-pyrrolo[2,1-c][1,4]benzodiazepine-10(11H)-yl carbonyl)-2-pyridinyl]benzamide (CL-385004) and analogs as orally active arginine vasopressin receptor antagonists", Bioorganic & Medicinal Chemistry Letters, 1999, pp. 1737-1740, vol. 9 No. 13.

Dayan, et al, Effects of Isoxazole Herbicides on Protoporhyrinogen Oxidase and Porphyrin Physiology, J. Agric. Food Chem., 1997, vol. 45, 967-975.

Gaede, et al, Novel Perfluoroalkyl-Substituted Pyrazoles. 1. Hydroxypyrazoles, J. Heterocyclic Chem., 1993, vol. 30, 49-54.

Hamper, Regioselective Synthesis of 1-Methyl-3-Hydroxy-5-Perfluoroalkykpyrazoles by the addition of Methylhydrazine to Perfluoroalklacetylenic Esters, Journal of Flourine Chemistry, 1990, vol. 48, 123-131.

Hamper, et al, Cyclocondensation of Alkyhydrazines and beta-substituted Acetylenic Esters: Synthesis of 3-Hydroxypyrazoles, J. Org. Chem, 1992, vol. 57, 5680-5686.

Hamper, et al, Synthesis of Chiral Substituted Phenyl(Trifluoromethyl)Pyrazole Herbicides, American Chemical Society, 216th ACS National Meeting, Ab. 290, Boston, MA, Aug. 23-27, 1998.

Hamper, et al, Chiral 3-Aryl-4-halo-5-(trifluoromethyl)pyrazoles , Synthesis and Herbicidal Activity of Enantiomeric Lactate Derivatives of Aryl-Pyrazole Herbicides, ACS Symposium Series, 2000, 746 (Asymmetric Fluororganic Chemistry) 272-281.

Prosch, et al, JV 485: A New Herbicide for Pre-Emergence Broad Spectrum Weed Control in Winter Wheat, The 1997 Brighton Crop Protection Conference—Weeds, 2-5, 45-50.

Zhou, et al, Synthesis and Herbicidal Activities of 3-(Substituted phenyl)isoxazole Derivatives, Chinese Chemical Letters, 2003, vol. 14, No. 9, 897-900.

* cited by examiner

BENZAMIDE INHIBITORS OF THE P2X₇ RECEPTOR

CROSS-REFERENCES TO RELATED APPLICATIONS

This application is a continuation of U.S. application Ser. No. 10/844,251, filed May 12, 2004, now allowed, which claims benefit of priority from U.S. Provisional Patent application Ser. No. 60/470,001, filed on May 12, 2003.

BACKGROUND OF THE INVENTION

The present invention relates to novel benzamide inhibitors of the P2X$_7$ receptor, processes for their preparation, intermediates useful in their preparation, pharmaceutical compositions containing them, and their use in therapy. The active compounds of the present invention are useful in the treatment of inflammatory diseases such as osteoarthritis and rheumatoid arthritis; allergies, asthma, COPD, cancer, reperfusion or ischemia in stroke or heart attack, autoimmune diseases and other disorders. The active compounds are also antagonists of the P2X$_7$ receptor.

The P2X$_7$ receptor (previously known as P2Z receptor), which is a ligand-gated ion channel, is present on a variety of cell types, largely those known to be involved in inflammatory/immune process, specifically, macrophages, mast cells and lymphocytes (T and B). Activation of the P2X$_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis, and L-selectin shedding (lymphocytes). P2X$_7$ receptors are also located on antigen-presenting cells (APC), keratinocytes, salivary acinar cells (parotid cells), hepatocytes and mesangial cells.

P2X$_7$ antagonists are known in the art, such as those described in International Patent Publications WO 01/46200, WO 01/42194, WO 01/44213, WO 99/29660, WO 00/61569, WO 99/29661, WO 99/29686, WO 00/71529, and WO 01/44170. Other inhibitors of P2X$_7$ are described in United States Non-provisional application Ser. No. 10/292,887, filed Nov. 12, 2002, which claimed priority to U.S. Provisional Application 60/336,781, filed Nov. 12, 2001. Other adamantyl P2X$_7$ inhibitors are described in U.S. Non-provisional application Ser. No. 10/292,886 filed Nov. 12, 2002 which claimed priority to U.S. provisional application 60/336,892 filed Nov. 12, 2001. Yet other P2X$_7$ inhibitors are described in U.S. Provisional Applications 60/437,228 and 60/437,505 both filed Dec. 31, 2002. Each of the foregoing application is incorporated herein by reference in their entirety.

Benzamides, heteroarylamides and reverse amides for uses other than inhibition of the P2X$_7$ receptor are described in various publications, such as International Patent Publications WO 97/22600, EP 138,527, WO 00/71509, WO 98/28269, WO 99/17777 and WO 01/58883.

SUMMARY OF THE INVENTION

In one aspect, the present invention relates to compounds of the formula

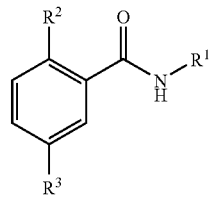

I wherein R$^1$ is a (C$_1$-C$_6$)alkyl optionally substituted with one or two radicals independently selected from hydroxy, halo, —CN, (C$_1$-C$_6$)alkyl, HO(C$_1$-C$_6$)alkyl, NH$_2$(C=O)—, (C$_1$-C$_6$)alkyl-NH—(C=O)—, [(C$_1$-C$_6$)alkyl]$_2$N—(C=O)—, oxo and (C$_1$-C$_6$)alkoxy;

wherein said R$^1$ (C$_1$-C$_6$)alkyl may also optionally be substituted with one or two groups independently selected from (C$_1$-C$_6$)alkyl, (C$_3$-C$_{10}$)cycloalkyl, (C$_6$-C$_{10}$)aryl and (C$_1$-C$_{10}$)heteroaryl; wherein said (C$_3$-C$_{10}$)cycloalkyl group is other than adamantyl; wherein said (C$_1$-C$_6$)alkyl and (C$_3$-C$_{10}$)cycloalkyl may be optionally substituted with oxo; wherein said (C$_1$-C$_{10}$)heteroaryl is selected from furanyl, thiophenyl, benzthiophenyl, benzfuranyl and chromanyl; wherein each of said (C$_1$-C$_6$)alkyl, (C$_3$-C$_{10}$)cycloalkyl, (C$_6$-C$_{10}$)aryl and (C$_1$-C$_{10}$)heteroaryl groups may also optionally be substituted by one to three radicals independently selected from hydroxy, halo, —CN, (C$_1$-C$_6$)alkyl, HO(C$_1$-C$_6$)alkyl, NH$_2$(C=O)—, (C$_1$-C$_6$)alkyl-NH(C=O)—, [(C$_1$-C$_6$)alkyl]$_2$N—(C=O)—, (C$_1$-C$_6$)alkoxy, (C$_6$-C$_{10}$)aryl and (C$_3$-C$_{10}$)cycloalkyl; wherein said (C$_3$-C$_{10}$)cycloalkyl and (C$_6$-C$_{10}$)aryl radicals are optionally substituted by one to three moieties independently selected from halo, (C$_1$-C$_6$)alkyl, —CN and (C$_1$-C$_6$)alkoxy;

R$^2$ is halo, —CN or (C$_1$-C$_6$)alkyl; wherein said (C$_1$-C$_6$)alkyl is optionally substituted by one to three radicals independently selected from the group consisting of: halo, hydroxy, amino, —CN, (C$_1$-C$_6$)alkyl, (C$_1$-C$_6$)alkoxy, —CF$_3$, CF$_3$O—, NH$_2$, (C$_1$-C$_6$)alkyl-NH—, [(C$_1$-C$_6$)alkyl]$_2$—N—, (C$_1$-C$_6$)alkyl-S—, (C$_1$-C$_6$)alkyl-(S=O)—, (C$_1$-C$_6$)alkyl-(SO$_2$)—, (C$_1$-C$_6$)alkyl-O—(C=O)—, formyl, (C$_1$-C$_6$)alkyl-(C=O)—, and (C$_3$-C$_6$)cycloalkyl;

R$^3$ is an optionally substituted carbon linked (C$_1$-C$_{10}$)heteroaryl or (C$_1$-C$_{10}$)heterocyclyl; wherein said optional substituents can be on any carbon atom of said (C$_1$-C$_{10}$)heteroaryl or (C$_1$-C$_{10}$)heterocyclyl capable of substitution with one to three R$^4$ per ring; wherein said optional substituents can be on any nitrogen atom of said (C$_1$-C$_{10}$)heteroaryl or (C$_1$-C$_{10}$)heterocyclyl capable of substitution with one to two R$^5$ per ring;

wherein each R$^4$ is independently selected from the group consisting of: halo, —CN, NH$_2$, hydroxy, H$_2$N(C=O)—, H$_2$N—SO$_2$—, and optionally substituted R$^6$ substituents;

wherein said optionally substituted R$^6$ substituents are selected from the group consisting of: (C$_1$-C$_6$)alkyl, (C$_3$-C$_{10}$)cycloalkyl, (C$_1$-C$_{10}$)heterocyclyl, (C$_6$-C$_{10}$)aryl, (C$_1$-C$_{10}$)heteroaryl, (C$_1$-C$_6$)alkoxy, (C$_1$-C$_6$)

alkyl-(C=O)O—, $(C_1-C_6)$alkyl-NH—, $[(C_1-C_6)$alkyl$]_2$—N—, $(C_6-C_{10})$aryl-NH—, $(C_1-C_6)$alkyl-(C=O)NH—, $(C_1-C_6)$alkyl-SO$_2$—NH—, $(C_1-C_6)$alkyl-(C=O)—, $(C_1-C_6)$alkyl-NH—(C=O)—, $[(C_1-C_6)$alkyl$]_2$—N—(C=O)—, $(C_1-C_6)$alkyl-O(C=O)—, $(C_3-C_{10})$cycloalkyl-(C=O)—, $(C_1-C_{10})$heterocyclyl-(C=O)—, $(C_6-C_{10})$aryl-(C=O)—, $(C_1-C_{10})$heteroaryl-(C=O)—, $(C_1-C_6)$alkyl-SO$_2$—, $(C_6-C_{10})$aryl-SO$_2$—, $(C_1-C_{10})$heteroaryl-SO$_2$—, $(C_1-C_6)$alkyl-NH—SO$_2$—, and $[(C_1-C_6)$alkyl$]_2$N—SO$_2$—;

wherein any two $R^4$ radicals on a carbon atom of said $(C_1-C_{10})$heterocycyl can be taken together to form an oxo group or a spiro $(C_3-C_6)$carbocyclic or $(C_1-C_6)$ heterocyclic group;

wherein each $R^5$ is independently selected from the group consisting of: $H_2N(C=O)$—, and the following optionally substituted $R^8$ groups: $(C_1-C_6)$alkyl, $(C_1-C_{10})$heterocyclyl, $(C_1-C_{10})$heteroaryl, $(C_1-C_6)$alkyl-(C=O)—, $(C_1-C_6)$alkyl-NH—(C=O)—, $[(C_1-C_6)$alkyl$]_2$—N—(C=O)—, $(C_1-C_6)$alkyl-O(C=O)—, $(C_3-C_{10})$cycloalkyl-(C=O)—, $(C_1-C_{10})$heterocyclyl-(C=O)—, $(C_6-C_{10})$aryl-(C=O)—, $(C_1-C_{10})$heteroaryl-(C=O)—, and $(C_1-C_6)$alkyl-SO$_2$—;

wherein each of said optionally substituted $R^6$ substituents may be substituted with one to three groups independently selected from the group consisting of: halo, $NH_2$, —CN, hydroxy, $(C_1-C_6)$alkyl-SO$_2$—, $H_2N$—SO$_2$—, $(C_1-C_6)$alkyl-NH—SO$_2$—, and $[(C_1-C_6)$alkyl$]_2N$—SO$_2$—, $(C_1-C_6)$alkoxy, $(C_1-C_6)$alkyl-SO$_2$—NH—, $(C_1-C_6)$alkyl-(C=O)—, $(C_1-C_6)$alkyl-(C=O)O—, $H_2N(C=O)$—, $(C_1-C_6)$alkyl-NH—(C=O)—, $[(C_1-C_6)$alkyl$]_2$—N—(C=O)—, $(C_1-C_6)$alkyl-O(C=O)—, and optionally substituted $R^7$ groups;

wherein each of said optionally substituted $R^7$ groups are independently selected from the group consisting of: $(C_3-C_{10})$cycloalkyl, $(C_1-C_{10})$heterocyclyl, $(C_6-C_{10})$aryl, $(C_1-C_{10})$heteroaryl, phenoxy, $(C_1-C_6)$alkyl-NH—, $[(C_1-C_6)$alkyl$]_2$—N—, $(C_6-C_{10})$aryl-NH—, $(C_3-C_{10})$cycloalkyl-(C=O)—, $(C_1-C_{10})$heterocyclyl-(C=O)—, $(C_6-C_{10})$aryl-(C=O)—, $(C_1-C_{10})$heteroaryl-(C=O)—, $(C_6-C_{10})$aryl-SO$_2$—, and $(C_1-C_{10})$heteroaryl-SO$_2$—;

wherein each of said optionally substituted $R^7$ groups may be optionally substituted with one to three substituents independently selected from the group consisting of: halo, $CF_3$, —CN, $(C_1-C_6)$alkyl, $(C_1-C_{10})$heterocyclyl, $(C_1-C_{10})$heteroaryl, hydroxy, $(C_1-C_6)$alkoxy, $(C_1-C_6)$alkyl-O(C=O)—, $(C_1-C_6)$alkyl-SO$_2$—NH—, $(C_1-C_6)$alkyl-SO$_2$—, $(C_6-C_{10})$aryl-SO$_2$—, $(C_1-C_{10})$heteroaryl-SO$_2$—, $H_2N$—SO$_2$—, $(C_1-C_6)$alkyl-NH—SO$_2$—, and $[(C_1-C_6)$alkyl$]_2N$—SO$_2$—;

wherein each of said optionally substituted $R^8$ groups may be substituted with one to three substituents may be independently selected from the group consisting of: halo, —CN, hydroxy, $(C_1-C_6)$alkoxy, $(C_1-C_6)$alkyl-(C=O)O—, $H_2N$—(C=O)O—, $(C_1-C_6)$alkyl-NH—(C=O)O—, $((C_1-C_6)$alkyl$)_2N$—(C=O)O—, $NH_2$, $(C_1-C_6)$alkyl-NH—, $[(C_1-C_6)$alkyl$]_2$—N—, $(C_1-C_6)$alkyl)-(C=O)NH—, $(C_1-C_6)$alkyl)-NH—(C=O)NH—, $(C_1-C_6)$alkyl-SO$_2$—NH—, $(C_1-C_6)$alkyl-(C=O)NH—, $(C_1-C_6)$alkyl-(C=O)—, $H_2N$(C=O)—, $(C_1-C_6)$alkyl-NH—(C=O)—, $[(C_1-C_6)$alkyl$]_2$—N—(C=O)—, $(C_1-C_6)$alkyl-O(C=O)—, $(C_1-C_6)$alkyl-SO$_2$—, $H_2N$—SO$_2$—, $(C_1-C_6)$alkyl-NH—SO$_2$—, and $[(C_1-C_6)$alkyl$]_2N$—SO$_2$— and optionally substituted $R^9$ groups;

wherein each of said optionally substituted $R^9$ groups are independently selected from the group consisting of: $(C_6-C_{10})$aryl, $(C_3-C_{10})$cycloalkyl-NH(C=O)—, $(C_1-C_{10})$heterocyclyl-NH—(C=O)—, $(C_6-C_{10})$aryl-NH—(C=O)—, $(C_1-C_{10})$heteroaryl-NH—(C=O)—, $(C_3-C_{10})$cycloalkyl-(C=O)—, $(C_1-C_{10})$heterocyclyl-(C=O)—, $(C_6-C_{10})$aryl-(C=O)—, $(C_1-C_{10})$heteroaryl-(C=O)—, $(C_6-C_{10})$aryl-SO$_2$—, $(C_1-C_{10})$heteroaryl-SO$_2$—;

wherein each of said optionally substituted $R^9$ groups may be optionally substituted with one to three substituents independently selected from the group consisting of: halo, $(C_1-C_6)$alkyl, —CN, hydroxy, $(C_1-C_6)$alkoxy, $(C_1-C_6)$alkyl-(C=O)O—, $NH_2$, $(C_1-C_6)$alkyl-NH—, $[(C_1-C_6)$alkyl$]_2$—N—, $((C_1-C_6)$alkyl)-(C=O)NH—, $(C_1-C_6)$alkyl-(C=O)—, $H_2N$(C=O)—, $(C_1-C_6)$alkyl-NH—(C=O)— and $[(C_1-C_6)$alkyl$]_2$—N—(C=O)—;

wherein the molecular weight of said compound of formula I is less than 700 AMU; or a pharmaceutically acceptable salt thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

This invention also encompasses pharmaceutical compositions containing prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

This invention also encompasses compounds of formula I containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds. One example of a tautomeric structure is when $R^3$ is a group of the formula

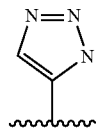

One skilled in the art will appreciate that this group can also be drawn as its tautomer

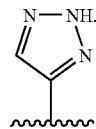

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

As used herein, the term "spiro" refers to a connection between two groups, substituents etc., wherein the connection occurs at the same carbon atom such as can be depicted according to the following formula

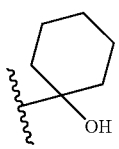

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_6)$alkyl, more preferred are $(C_1-C_4)$alkyl, and most preferred are methyl and ethyl.

As used herein, the term "cycloalkyl" refers to a mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "halogen" includes fluoro, chloro, bromo or iodo or fluoride, chloride, bromide or iodide.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "oxo" is used herein to mean a double bonded oxygen (=O) radical wherein the bond partner is a carbon atom. Such a radical can also be thought as a carbonyl group.

As used herein, the term "aryl" means aromatic radicals such as phenyl, naphthyl, tetrahydronaphthyl, indanyl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred $R^3$ heteroaryl groups include oxazolyl, imidazolyl, pyridyl, thienyl, furyl, thiazolyl, pyridazinyl and pyrazolyl.

The term "heterocyclic" or "heterocyclyl" as used herein refers to a cyclic group containing 1-10 carbon atoms and 1 to 4 hetero atoms selected from N, O, $S(O)_n$ or NR (wherein "R" is a suitable substituent as defined above). A heterocyclic group may include a mono bicyclic or tricyclic ring having 1-10 carbon atoms and 1-4 hetero atoms selected from N, O $S(O)_n$ or NR. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally containing 1 or 2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Preferred $R^3$ heterocyclics include tetrahydrofuranyl, pyrrolidinyl, piperidinyl, piperazinyl and morpholinyl.

Nitrogen heteroatoms as used herein refers to N=, >N and —NH; wherein —N= refers to a nitrogen double bond; >N refers to a nitrogen containing two bond connections and —N refers to a nitrogen containing one bond.

"Embodiment" as used herein refers to specific groupings of compounds or uses into discrete subgenera. Such subgenera may be cognizable according to one particular substituent such as a specific $R^1$ or $R^3$ group. Other subgenera are cognizable according to combinations of various substituents, such as all compounds wherein $R^2$ is chloro and $R^1$ is $(C_1-C_4)$alkyl, optionally substituted by $(C_3-C_{10})$cycloalkyl. The phrase "in combination with each of the aforementioned embodiments" refers to combinations of the identified embodiment with each embodiment previously identified in the specification. Thus an embodiment of compounds wherein $R^1$ is $(C_1-C_4)$alkyl, optionally substituted by $(C_3-C_{10})$cycloalkyl "in combination with each of the aforementioned embodiments" refers to additional embodiments comprising combinations with each embodiment previously identified in the specification.

One embodiment of the invention includes compounds of formula (I) in which $R^2$ is halogen and $(C_1-C_6)$alkyl, and preferably compounds in which $R^2$ is chloro, methyl or ethyl.

Another embodiment of the invention includes compounds of formula (I) wherein $R^1$ is $(C_1-C_{12})$alkyl optionally substituted by one to six (preferably one to three) radicals independently selected from the group consisting of: hydroxy, halogen, —CN, $(C_1-C_6)$alkyl, HO$(C_1-C_6)$alkyl, $(C_1-C_6)$alkyl-NH(C=O)—, NH$_2$(C=O)— and $(C_1-C_6)$alkoxy.

Another embodiment of the invention includes compounds of formula (I) wherein $R^1$ is optionally substituted $(C_1-C_2)$alkyl.

Another embodiment of the invention includes compounds of formula (I) wherein $R^1$ is $(C_1-C_4)$alkyl substituted with one or two (preferably one) $(C_3-C_{10})$cycloalkyl; wherein said $(C_1-C_4)$alkyl (more preferably $(C_1-C_2)$alkyl) is also optionally substituted by one to three radicals independently selected from the group consisting of: hydroxy, halogen, —CN, $(C_1-C_6)$alkyl, HO$(C_1-C_6)$alkyl, $(C_1-C_6)$alkyl-NH(C=O)—, NH$_2$(C=O)— and $(C_1-C_6)$alkoxy; wherein said $(C_3-C_{10})$cycloalkyl is optionally substituted by one to three radicals independently selected from hydroxy, halogen, —CN, $(C_1-C_6)$alkyl, HO$(C_1-C_6)$alkyl, $(C_1-C_6)$alkyl-NH(C=O)—, NH$_2$(C=O)—, $(C_1-C_6)$alkoxy and $(C_3-C_{10})$cycloalkyl; wherein said $(C_3-C_{10})$cycloalkyl radical is optionally substituted by one to three moieties independently selected from halogen and $(C_1-C_6)$alkyl.

Another embodiment of the invention includes those compounds of formula (I) wherein $R^1$ is $(C_1-C_4)$alkyl (more preferably $(C_1-C_2)$alkyl) substituted with one or two (preferably one) $(C_3-C_{10})$cycloalkyl; wherein said $(C_3-C_{10})$cycloalkyl is spiro substituted at the $(C_1-C_4)$alkyl linkage by a radical selected from the group consisting of: hydroxy, halogen, —CN, $(C_1-C_6)$alkyl, HO$(C_1-C_6)$alkyl, $(C_1-C_6)$alkyl-NH(C=O)—, NH$_2$(C=O)—, $(C_1-C_6)$alkoxy and $(C_6-C_{10})$aryl.

Another embodiment of the invention includes those compounds of formula (I) wherein $R^1$ is $(C_1-C_4)$alkyl substituted with one or two (preferably one) $(C_6-C_{10})$aryl; wherein said $(C_1-C_4)$alkyl (more preferably $(C_1-C_2)$alkyl) is also optionally substituted by one to three radicals independently selected from the group consisting of: hydroxy, halogen, —CN, $(C_1-C_6)$alkyl, HO$(C_1-C_6)$alkyl, $(C_1-C_6)$alkyl-NH(C=O)—, H$_2$N(C=O)— and $(C_1-C_6)$alkoxy; wherein said $(C_6-C_{10})$aryl is optionally substituted by one to three radicals independently selected from hydroxy, halogen, —CN, $(C_1-C_6)$alkyl, HO$(C_1-C_6)$alkyl, $(C_1-C_6)$alkyl-NH(C=O)—, NH$_2$(C=O)—, $(C_1-C_6)$alkoxy and $(C_3-C_{10})$cycloalkyl; wherein said $(C_3-C_{10})$cycloalkyl radical is optionally substituted by one to three moieties independently selected from halogen and $(C_1-C_6)$alkyl.

Another embodiment of the invention includes those compounds of formula (I) wherein $R^1$ is $(C_1-C_4)$alkyl substituted with one or two (preferably one) $(C_1-C_{10})$heteroaryl; wherein said $(C_1-C_4)$alkyl (more preferably $(C_1-C_2)$alkyl) is also optionally substituted by one to three radicals independently selected from the group consisting of: hydroxy, halogen, —CN, $(C_1-C_6)$alkyl, HO$(C_1-C_6)$alkyl, $(C_1-C_6)$alkyl-NH(C=O)—, NH$_2$(C=O)— and $(C_1-C_6)$alkoxy; wherein said $(C_1-C_{10})$heteroaryl is optionally substituted by one to three radicals independently selected from hydroxy, halogen, —CN, $(C_1-C_6)$alkyl, HO$(C_1-C_6)$alkyl, $(C_1-C_6)$alkyl-NH(C=O)—, NH$_2$(C=O)—, $(C_1-C_6)$alkoxy and $(C_3-C_{10})$cycloalkyl; wherein said $(C_3-C_{10})$cycloalkyl radical is optionally substituted by one to three moieties independently selected from halogen and $(C_1-C_6)$alkyl.

Another embodiment of the invention are compounds of formula (I) in which $R^3$ is a carbon linked $(C_1-C_{10})$heteroaryl or $(C_1-C_{10})$heterocyclyl optionally substituted on any carbon or nitrogen atom capable of substitution with one to three $R^4$ independently selected from the group consisting of: hydrogen, hydroxy, halogen, and —CN; more preferably one or two $R^4$ per ring; wherein one of said $R^4$ is hydrogen, —CN or halo.

In certain embodiment of formula I are compounds wherein $R^2$ is halo or $(C_1-C_6)$alkyl. In certain embodiment of formula I are compounds wherein $R^1$ is $(C_1-C_2)$alkyl substituted with one or two $(C_3-C_{10})$cycloalkyl; wherein said $(C_1-C_2)$alkyl is also optionally substituted by one to three radicals independently selected from the group consisting of: hydroxy, halo, —CN, $(C_1-C_6)$alkyl, HO$(C_1-C_6)$alkyl, $(C_1-C_6)$alkyl-NH(C=O)—, NH$_2$(C=O)— and $(C_1-C_6)$alkoxy; wherein said $(C_3-C_{10})$cycloalkyl is optionally substituted by one to three radicals independently selected from: hydroxy, halo, —CN, $(C_1-C_6)$alkyl, HO$(C_1-C_6)$alkyl, $(C_1-C_6)$alkyl-NH(C=O)—, NH$_2$(C=O)—, $(C_1-C_6)$alkoxy and $(C_3-C_{10})$cycloalkyl; and said $(C_3-C_{10})$cycloalkyl may be optionally spiro substituted at the (C₁-C₂)alkyl linkage by a radical selected from the group consisting of: hydroxy, halo, —CN, (C₁-C₆)alkyl, HO(C₁-C₆)alkyl, (C₁-C₆)alkyl-NH(C=O)—, NH₂(C=O)—, (C₁-C₆)alkoxy and (C₆-C₁₀)aryl.

In certain embodiment of formula I are compounds wherein R³ is a carbon linked (C₁-C₁₀)heteroaryl or (C₁-C₁₀) heterocyclyl substituted on a carbon atom capable of substitution with one to three R⁴; wherein said R⁴ is (C₁-C₆)alkoxy or phenoxy; wherein R⁴ is optionally substituted with one to three substituents independently selected from the group consisting of: halo, hydroxy, —CN, —NH₂, and (C₁-C₆)alkoxy and optionally substituted R⁶ substituents selected from the group consisting of: (C₁-C₆)alkyl-(C=O)— and (C₁-C₆) alkyl-O(C=O)—; or wherein R⁴ is optionally substituted with a (C₁-C₁₀)heterocyclyl that may be optionally substituted with 1 substituent selected from the group consisting of: halo, CF₃, —CN, (C₁-C₆)alkyl, hydroxy, (C₁-C₆)alkoxy, (C₁-C₆)alkyl-O(C=O)—, (C₁-C₆)alkyl-SO₂—, H₂N—SO₂—, [(C₁-C₆)alkyl]NH—SO₂—, [(C₁-C₆)alkyl]₂N—SO₂—, (C₁-C₆)alkyl-NH—, [(C₁-C₆)alkyl]₂—N—, (C₆-C₁₀)aryl-NH—, NH₂(C=O)—, (C₁-C₆)alkyl-NH—(C=O)— and [(C₁-C₆)alkyl]₂—N—(C=O)—.

In certain embodiment of formula I are compounds wherein R³ is a carbon linked (C₁-C₁₀)heteroaryl or (C₁-C₁₀) heterocyclyl substituted on any carbon atom capable of substitution with one to three optionally substituted R⁶ substituents independently selected from the group consisting of: (C₃-C₁₀)cycloalkyl, (C₁-C₁₀)heterocyclyl, (C₆-C₁₀)aryl, and (C₁-C₁₀)heteroaryl.

In certain embodiment of formula I are compounds wherein R³ is a carbon linked (C₁-C₁₀)heteroaryl or (C₁-C₁₀) heterocyclyl substituted on any carbon atom capable of substitution with one R⁴ selected from the group consisting of: H₂NSO₂—, and an optionally substituted R⁶ substituent selected from the group consisting of: (C₁-C₆)alkyl-SO₂—, (C₁-C₆)alkyl-NH—SO₂— and ((C₁-C₆)alkyl)₂N—SO₂—.

In certain embodiment of formula I are compounds wherein R³ is a carbon linked (C₁-C₁₀)heteroaryl or (C₁-C₁₀) heterocyclyl substituted on any nitrogen atom capable of substitution with one R⁵ per ring; wherein R⁵ is a (C₁-C₆) alkyl- which may be optionally substituted with one to three substituents independently selected from the group consisting of: halo, —CN, hydroxy, (C₁-C₆)alkoxy, (C₁-C₆)alkyl-(C=O)O—, H₂N—(C=O)O—, (C₁-C₆)alkyl-NH—(C=O)O—, ((C₁-C₆)alkyl)₂N—(C=O)O—, NH₂, (C₁-C₆)alkyl-NH—, [(C₁-C₆)alkyl]₂—N—, (C₁-C₆)alkyl)-(C=O) NH—, (C₁-C₆)alkyl)-NH—(C=O)NH—, (C₁-C₆)alkyl-(C=O)—, H₂N(C=O)—, [(C₁-C₆)alkyl]₂—N—(C=O)—, (C₁-C₆)alkyl-O(C=O)—, and an optionally substituted R⁹ selected from the group consisting of: (C₆-C₁₀)aryl, (C₁-C₆) alkyl-NH—(C=O)—, (C₃-C₁₀)cycloalkyl-NH(C=O)—, (C₁-C₁₀)heterocyclyl-NH—(C=O)—, (C₆-C₁₀)aryl-NH—(C=O)—, (C₁-C₁₀)heteroaryl-NH—(C=O)—, (C₃-C₁₀)cycloalkyl-(C=O)—, (C₁-C₁₀)heterocyclyl-(C=O)—, (C₆-C₁₀)aryl-(C=O)— and (C₁-C₁₀)heteroaryl-(C=O)—; wherein said optionally substituted R⁹ may be substituted with one to three substituents independently selected from the group consisting of: halo, (C₁-C₆)alkyl, hydroxy, (C₁-C₆) alkoxy, NH₂, (C₁-C₆)alkyl-NH—, [(C₁-C₆)alkyl]₂—N—, H₂N(C=O)—, (C₁-C₆)alkyl-NH—(C=O)— and [(C₁-C₆) alkyl]₂—N—(C=O)—.

In certain embodiment of formula I are compounds wherein R³ is a suitably substituted five-membered carbon linked (C₁-C₅)heterocyclyl of formula II(a)-II(j):

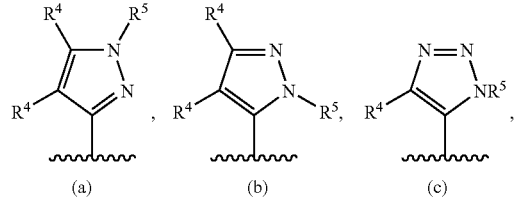

Formula II(a)-II(j)

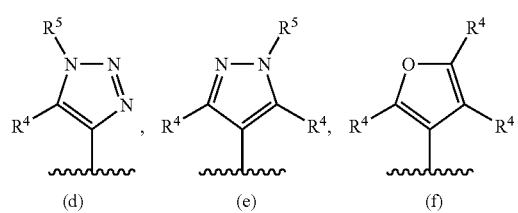

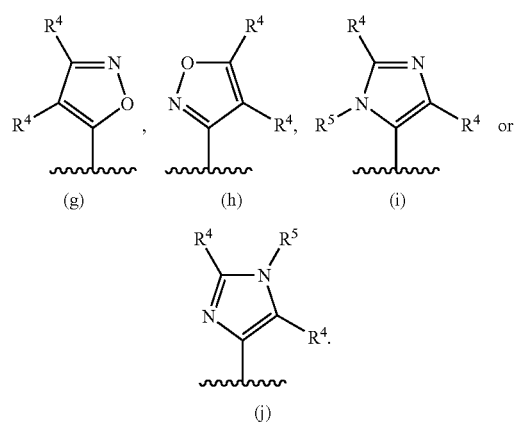

In certain embodiment of formula I are compounds wherein R³ is a six-membered carbon linked (C₁-C₆)heterocyclyl of formula III(a)-III(h), containing one to three R⁴ substitutents:

Formula III(a)-III(h)

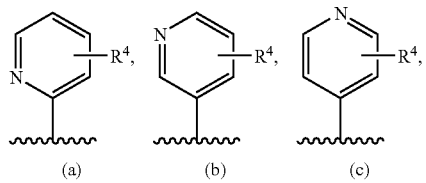

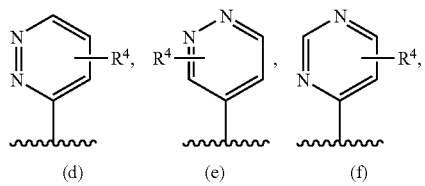

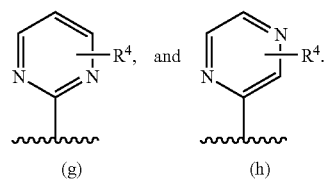

In certain embodiment of formula I are compounds wherein $R^3$ is a fused bicyclic carbon linked ($C_1$-$C_{10}$)heterocyclyl of formula IV(a)-IV(n), containing one to three $R^4$:

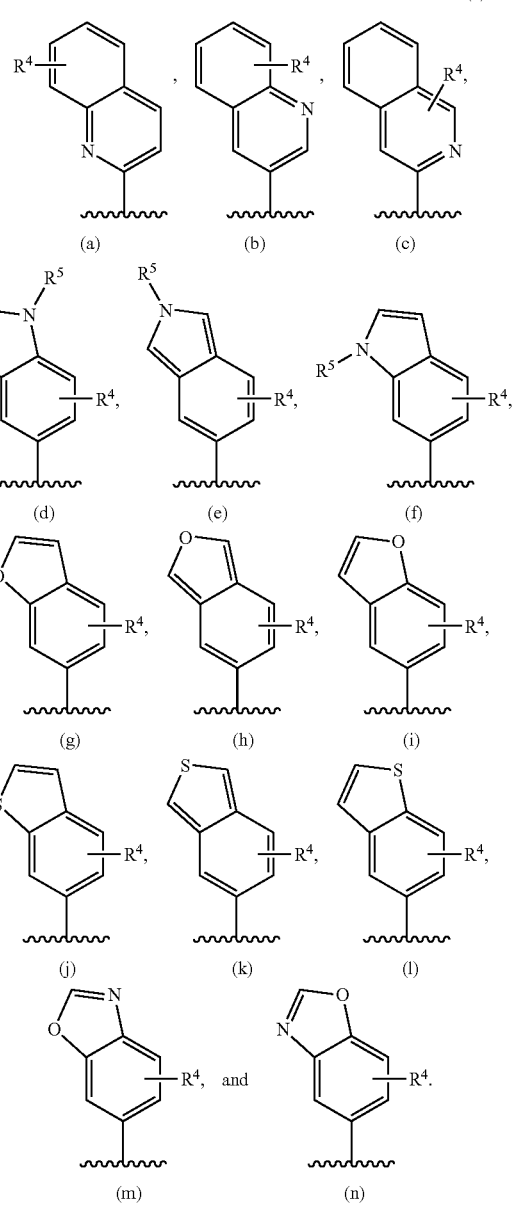

In certain embodiment of formula I are compounds wherein $R^3$ is a suitably substituted oxo substituted, carbon linked ($C_1$-$C_{10}$)heterocyclyl of formula V(a)-V(d):

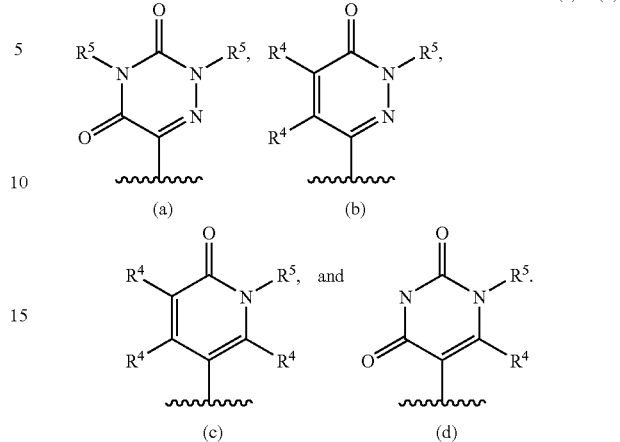

In certain embodiment of formula I are compounds of formula XXIX.

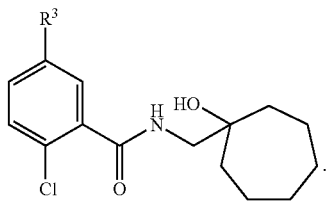

In certain embodiments of formula XXIX are compounds wherein $R^3$ is a suitably substituted five-membered carbon linked ($C_1$-$C_5$)heterocyclyl of formula II(a)-II(j).

Examples of preferred compounds of formula I are the following:

2-Chloro-5-[1-(2,3-dihydroxy-propyl)-5-methyl-1H-pyrazol-3-yl]-N-(1-hydroxy-cycloheptylmethyl)-benzamide;

2-Chloro-N-(1-hydroxy-cycloheptylmethyl)-5-[1-(2-hydroxy-3-methoxy-propyl)-5-methyl-1H-pyrazol-3-yl]-benzamide;

5-[1-(2-Amino-ethyl)-1H-pyrazol-3-yl]-2-chloro-N-(1-hydroxy-cycloheptylmethyl)-benzamide;

5-[1-(2-Amino-ethyl)-5-methyl-1H-pyrazol-3-yl]-2-chloro-N-(1-hydroxy-cycloheptylmethyl)-benzamide;

2-Chloro-N-(1-hydroxy-cycloheptylmethyl)-5-[1-(2-hydroxy-ethyl)-5-methyl-1H-pyrazol-3-yl]-benzamide;

2-Chloro-5-(5-ethyl-2H-pyrazol-3-yl)-N-(1-hydroxy-cycloheptylmethyl)-benzamide;

2-Chloro-N-(1-hydroxy-cycloheptylmethyl)-5-(5-methyl-2H-pyrazol-3-yl)-benzamide;

2-Chloro-5-(5-methyl-pyridin-2-yl)-N-(1-p-tolyl-cyclohexylmethyl)-benzamide;

2-Chloro-5-(1H-pyrazol-3-yl)-N-(1-p-tolyl-cyclohexylmethyl)-benzamide;

2-Chloro-N-[2-(2-chloro-phenyl)-ethyl]-5-(6-oxo-1,6-dihydro-pyridazin-3-yl)-benzamide;

2-Chloro-N-(1-hydroxy-cycloheptylmethyl)-5-(6-oxo-1,6-dihydro-pyridazin-3-yl)-benzamide;

2-Chloro-N-[2-(2-chloro-phenyl)-ethyl]-5-(5-methyl-pyridin-2-yl)-benzamide;

2-Chloro-5-{1-[(2-dimethylamino-ethylcarbamoyl)-methyl]-5-methyl-1H-pyrazol-3-yl}-N-(1-hydroxy-cycloheptylmethyl)-benzamide;
2-Chloro-N-(1-hydroxy-cycloheptylmethyl)-5-{1-[(2-hydroxy-ethylcarbamoyl)-methyl]-5-methyl-1H-pyrazol-3-yl}-benzamide;
2-Chloro-N-(1-hydroxy-cycloheptylmethyl)-5-{1-[(2-hydroxy-1-methyl-ethylcarbamoyl)-methyl]-5-methyl-1H-pyrazol-3-yl}-benzamide;
2-Chloro-N-(1-hydroxy-cycloheptylmethyl)-5-{5-methyl-1-[(methylcarbamoylmethyl-carbamoyl)-methyl]-1H-pyrazol-3-yl}-benzamide;
2-Chloro-N-(1-hydroxy-cycloheptylmethyl)-5-{1-[(2-hydroxy-1-hydroxymethyl-ethylcarbamoyl)-methyl]-5-methyl-1H-pyrazol-3-yl}-benzamide;
2-Chloro-5-{1-[2-(3,4-dihydroxy-pyrrolidin-1-yl)-2-oxo-ethyl]-5-methyl-1H-pyrazol-3-yl}-N-(1-hydroxy-cycloheptylmethyl)-benzamide; and
5-[1-(3-Amino-2-hydroxy-propyl)-5-methyl-1H-pyrazol-3-yl]-2-chloro-N-(1-hydroxy-cycloheptylmethyl)-benzamide.

Certain specific compounds of the invention are those compounds identified in Examples 1-58.

Other specific compounds of the invention include:
2-Chloro-N-(1-hydroxy-cycloheptylmethyl)-5-[5-(2-hydroxy-ethyl)-2H-pyrazol-3-yl]-benzamide;
2-Chloro-N-(1-hydroxy-cyclooctylmethyl)-5-[5-(2-hydroxy-ethyl)-2H-pyrazol-3-yl]-benzamide;
2-Chloro-5-[5-(2-hydroxy-ethyl)-2H-pyrazol-3-yl]-N-(1-p-tolyl-cyclohexylmethyl)-benzamide;
2-Chloro-5-[5-(2-hydroxy-ethyl)-2H-pyrazol-3-yl]-N-(2-hydroxy-2-phenyl-ethyl)-benzamide;
2-Chloro-N-[2-(2-chloro-phenyl)-ethyl]-5-[5-(2-hydroxy-ethyl)-2H-pyrazol-3-yl]-benzamide;
2-Chloro-N-(1-hydroxy-3,3-dimethyl-cyclohexylmethyl)-5-[5-(2-hydroxy-ethyl)-2H-pyrazol-3-yl]-benzamide;
N-(1-Hydroxy-cycloheptylmethyl)-5-[5-(2-hydroxy-ethyl)-2H-pyrazol-3-yl]-2-methyl-benzamide;
N-(1-Hydroxy-cyclooctylmethyl)-5-[5-(2-hydroxy-ethyl)-2H-pyrazol-3-yl]-2-methyl-benzamide;
5-[5-(2-Hydroxy-ethyl)-2H-pyrazol-3-yl]-2-methyl-N-(1-p-tolyl-cyclohexylmethyl)-benzamide;
5-[5-(2-Hydroxy-ethyl)-2H-pyrazol-3-yl]-N-(2-hydroxy-2-phenyl-ethyl)-2-methyl-benzamideN-[2-(2-Chloro-phenyl)-ethyl]-5-[5-(2-hydroxy-ethyl)-2H-pyrazol-3-yl]-2-methyl-benzamide;
N-(1-Hydroxy-3,3-dimethyl-cyclohexylmethyl)-5-[5-(2-hydroxy-ethyl)-2H-pyrazol-3-yl]-2-methyl-benzamide;
5-[1-(3-Amino-2-hydroxy-2-methyl-propyl)-5-cyclopropyl-1H-pyrazol-3-yl]-2-chloro-N-(1-hydroxy-cycloheptylmethyl)-benzamide;
5-[1-(3-Amino-2-hydroxy-2-methyl-propyl)-5-methyl-1H-pyrazol-3-yl]-2-chloro-N-(1-hydroxy-cyclooctylmethyl)-benzamide;
5-[1-(3-Amino-2-hydroxy-2-methyl-propyl)-5-methyl-1H-pyrazol-3-yl]-2-chloro-N-(1-hydroxy-3,3-dimethyl-cyclohexylmethyl)-benzamide;
5-[1-(3-Amino-2-hydroxy-2-methyl-propyl)-5-cyclopropyl-1H-pyrazol-3-yl]-2-chloro-N-(1-hydroxy-3,3-dimethyl-cyclohexylmethyl)-benzamide;
5-[1-(3-Amino-2-hydroxy-2-methyl-propyl)-5-methyl-1H-pyrazol-3-yl]-2-chloro-N-(1-hydroxy-cycloheptylmethyl)-benzamide;
5-[1-(3-Amino-2-hydroxy-2-methyl-propyl)-5-cyclopropyl-1H-pyrazol-3-yl]-2-chloro-N-(1-hydroxy-cyclooctylmethyl)-benzamide;
5-[5-(2-Amino-ethyl)-2H-pyrazol-3-yl]-2-chloro-N-(1-hydroxy-cycloheptylmethyl)-benzamide;
5-(1-Azetidin-3-yl-5-methyl-1H-pyrazol-3-yl)-2-chloro-N-(1-hydroxy-cyclooctylmethyl)-benzamide;
5-(1-Azetidin-3-yl-5-methyl-1H-pyrazol-3-yl)-2-chloro-N-(2-hydroxy-2-phenyl-ethyl)-benzamide;
5-(1-Azetidin-3-yl-5-cyclopropyl-1H-pyrazol-3-yl)-2-chloro-N-(2-hydroxy-2-phenyl-ethyl)-benzamide;
5-(1-Azetidin-3-yl-5-cyclopropyl-1H-pyrazol-3-yl)-2-chloro-N-(1-phenyl-cyclohexylmethyl)-benzamide;
2-Chloro-N-(1-hydroxy-cycloheptylmethyl)-5-[1-(4-hydroxy-pyrrolidin-3-yl)-5-methyl-1H-pyrazol-3-yl]-benzamide;
2-Chloro-N-(1-hydroxy-3,3-dimethyl-cyclohexylmethyl)-5-[1-(4-hydroxy-pyrrolidin-3-yl)-5-methyl-1H-pyrazol-3-yl]-benzamide;
2-Chloro-5-[5-cyclopropyl-1-(4-hydroxy-pyrrolidin-3-yl)-1H-pyrazol-3-yl]-N-(1-hydroxy-3,3-dimethyl-cyclohexylmethyl)-benzamide;
2-Chloro-N-(1-hydroxy-cycloheptylmethyl)-5-[5-methyl-1-(2-oxo-pyrrolidin-3-yl)-1H-pyrazol-3-yl]-benzamide;
2-Chloro-N-(1-hydroxy-cycloheptylmethyl)-5-[5-methyl-1-(5-oxo-pyrrolidin-3-yl)-1H-pyrazol-3-yl]-benzamide;
2-Chloro-N-(1-hydroxy-cycloheptylmethyl)-5-(5-methyl-1-pyrimidin-4-yl-1H-pyrazol-3-yl)-benzamide;
2-Chloro-5-(5-cyclopropyl-1-pyrimidin-4-yl-1H-pyrazol-3-yl)-N-(1-hydroxy-cycloheptylmethyl)-benzamide;
2-Chloro-5-(5-cyclopropyl-1-pyrimidin-4-yl-1H-pyrazol-3-yl)-N-(1-hydroxy-3,3-dimethyl-cyclohexylmethyl)-benzamide;
2-Chloro-N-(1-hydroxy-cycloheptylmethyl)-5-[1-(2-hydroxy-ethyl)-5-oxo-4,5-dihydro-1H-[1,2,4]triazol-3-yl]-benzamide;
2-Chloro-5-[1-(2-hydroxy-ethyl)-5-oxo-4,5-dihydro-1H-[1,2,4]triazol-3-yl]-N-(1-phenyl-cyclohexylmethyl)-benzamide;
5-[1-(3-Amino-2-hydroxy-propyl)-5-oxo-4,5-dihydro-1H-[1,2,4]triazol-3-yl]-2-chloro-N-(1-hydroxy-cycloheptylmethyl)-benzamide2-Chloro-N-(1-hydroxy-cycloheptylmethyl)-5-[1,2,4]triazolo[4,3-a]pyridin-3-yl-benzamide;
5-[1-(3-Amino-2-hydroxy-propyl)-5-oxo-4,5-dihydro-1H-[1,2,4]triazol-3-yl]-2-chloro-N-(1-cyano-cycloheptylmethyl)-benzamide2-Chloro-N-[2-(2-chloro-phenyl)-ethyl]-5-[1-(2,3-dihydroxy-propyl)-1H-indazol-3-yl]-benzamide;
2-Chloro-5-[1-(2,3-dihydroxy-propyl)-1H-indazol-3-yl]-N-(1-p-tolyl-cyclohexylmethyl)-benzamide2-Chloro-N-(1-hydroxy-cycloheptylmethyl)-5-(1H-indazol-3-yl)-benzamide;
2-Chloro-5-[1-(2,3-dihydroxy-propyl)-1H-indazol-3-yl]-N-(1-hydroxy-cycloheptylmethyl)-benzamide5-[5-(2-Amino-ethoxy)-1-methyl-1H-pyrazol-3-yl]-2-chloro-N-(1-hydroxy-cycloheptylmethyl)-benzamide;
5-[1-(3-Amino-2-hydroxy-propyl)-5-hydroxy-1H-pyrazol-3-yl]-2-chloro-N-(1-hydroxy-cycloheptylmethyl)-benzamide; and
2-Chloro-N-(1-hydroxy-cycloheptylmethyl)-5-(5-hydroxy-1H-pyrazol-3-yl)-benzamide.

The present invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

The compounds of Formula I or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

The present invention relates to a method for treating an IL-1 mediated disease in a mammal, preferably a human, in need thereof, which comprises administering to said mammal an effective amount of a compound of formula I.

The present invention also relates to a method for treating an IL-1 mediated condition. As defined herein, an "IL-1 mediated condition" includes but is not limited to a disease or disorder selected from the group consisting of: arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic obstructive pulmonary disease, chronic pulmonary inflammatory disease, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neuro-degenerative disorders, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune disorders, Huntington's disease, diabetes, AIDS, cachexia, sepsis, septic shock, endotoxic shock, conjunctivitis shock, gram negative sepsis, toxic shock syndrome, cerebral malaria, cardiac and renal reperfusion injury, thrombosis, glomerularonephritis, graft vs. host reaction, allograft rejection, organ transplant toxicity, ulcerative colitis, or muscle degeneration, in a mammal, preferably a human, comprising administering to said mammal an amount of a compound to formula I, effective in treating such a condition.

The present invention relates to a pharmaceutical composition for the treatment of an IL-1 mediated disease in a mammal which comprises an effective amount of a compound according of formula I and a pharmaceutically acceptable carrier.

The present invention relates to a pharmaceutical composition for the treatment of an IL-1 mediated condition in a mammal, preferably a human, comprising an amount of a compound of formula I, effective in treating such a condition and a pharmaceutically acceptable carrier.

Preferably, the compounds of the invention are useful for the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukemia, diabetes, Alzheimer's disease, meningitis, osteoporosis, burn injury, ischemic heart disease, stroke and varicose veins.

The present invention also provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

The invention further provides a method of treating osteoarthritis which comprises administering a therapeutically effective amount of a compound of formula (i), or a pharmaceutically acceptable salt or solvate thereof, as hereinbefore defined to a patient.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

The invention also provides a method of treating an obstructive airways disease (e.g. asthma or COPD) which comprises administering to a patient a therapeutically effective amount of a compound of formula (I), or a pharmaceutically acceptable salt or solvate thereof, as hereinbefore defined to a patient, preferably a human.

The present invention also relates to a compound of the formula:

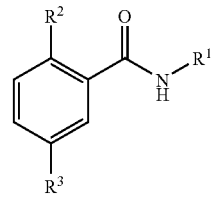

wherein $R^1$ is $(C_1$-$C_6)$alkyl optionally substituted with one or two radicals independently selected from hydroxy, halo, —CN, $(C_1$-$C_6)$alkyl, HO$(C_1$-$C_6)$alkyl, NH$_2$(C=O)—, $(C_1$-$C_6)$alkyl-NH—(C=O)—, [$(C_1$-$C_6)$alkyl]$_2$N—(C=O)—, oxo and $(C_1$-$C_6)$alkoxy;

wherein said $R^1$ $(C_1$-$C_6)$alkyl may also optionally be substituted with one or two groups independently selected from $(C_1$-$C_6)$alkyl, $(C_3$-$C_{10})$cycloalkyl, $(C_6$-$C_{10})$aryl and $(C_1$-$C_{10})$heteroaryl; wherein said $(C_3$-$C_{10})$cycloalkyl group is other than adamantyl; wherein said $(C_1-C_6)$alkyl and $(C_3-C_{10})$cycloalkyl may be optionally substituted with oxo; wherein said $(C_1-C_{10})$heteroaryl is selected from furanyl, thiophenyl, benzthiophenyl, benzfuranyl and chromanyl; wherein each of said $(C_1-C_6)$alkyl, $(C_3-C_{10})$cycloalkyl, $(C_6-C_{10})$aryl and $(C_1-C_{10})$heteroaryl groups may also optionally be substituted by one to three radicals independently selected from hydroxy, halogen, —CN, $(C_1-C_6)$alkyl, HO$(C_1-C_6)$alkyl, NH$_2$(C=O)—, $(C_1-C_6)$alkyl-NH(C=O)—, $[(C_1-C_6)$alkyl$]_2$N—(C=O)—, $(C_1-C_6)$alkoxy, $(C_6-C_{10})$aryl and $(C_3-C_{10})$cycloalkyl; wherein said $(C_3-C_{10})$cycloalkyl and $(C_6-C_{10})$aryl radicals are optionally substituted by one to three moieties independently selected from halogen, —CN, $(C_1-C_6)$alkyl and $(C_1-C_6)$alkoxy;

$R^2$ is halogen, —CN or $(C_1-C_6)$alkyl; wherein said $(C_1-C_6)$alkyl is optionally substituted by one to three radicals independently selected from the group consisting of: halo, hydroxy, amino, —CN, $(C_1-C_6)$alkyl, $(C_1-C_6)$alkoxy, —CF$_3$, CF$_3$O—, NH$_2$, $(C_1-C_6)$alkyl-NH—, $[(C_1-C_6)$alkyl$]_2$—N—, $(C_1-C_6)$alkyl-S—, $(C_1-C_6)$alkyl-(S=O)—, $(C_1-C_6)$alkyl-(SO$_2$)—, $(C_1-C_6)$alkyl-O—(C=O)—, formyl, $(C_1-C_6)$alkyl-(C=O)—, and $(C_3-C_6)$cycloalkyl;

$R^3$ is an optionally substituted carbon linked $(C_1-C_{10})$heteroaryl or $(C_1-C_{10})$heterocyclyl; wherein said optional substituents can be on any carbon atom of said $(C_1-C_{10})$heteroaryl or $(C_1-C_{10})$heterocyclyl capable of substitution with one to three $R^4$ per ring; wherein said optional substituents can be on any nitrogen atom of said $(C_1-C_{10})$heteroaryl or $(C_1-C_{10})$heterocyclyl capable of substitution with one to two $R^5$ per ring;

each $R^4$ is independently selected from the group consisting of: halogen, —CN, $(R^6)_n$—$(C_1-C_6)$alkyl, $(R^6)_n$—$(C_3-C_{10})$cycloalkyl, $(R^6)_n$—$(C_1-C_{10})$heterocyclyl, $(R^6)_n$—$(C_6-C_{10})$aryl, $(R^6)_n$—$(C_1-C_{10})$heteroaryl, hydroxy, $(R^6)_n$—$(C_1-C_6)$alkoxy, $(R^6)_n$—$(C_1-C_6)$alkyl-(C=O)O—; NH$_2$, $(R^6)_n$—$(C_1-C_6)$alkyl-NH—, $[(R^6)_n$—$(C_1-C_6)$alkyl$]_2$—N—, $(R^6)_n$—$(C_6-C_{10})$aryl-NH—, $(R^6)_n$—$(C_1-C_6)$alkyl-(C=O)NH—, $(R^6)_n$—$(C_1-C_6)$alkyl-SO$_2$—NH—, $(R^6)_n$—$(C_1-C_6)$alkyl-(C=O)—, H$_2$N(C=O)—, $(R^6)_n$—$(C_1-C_6)$alkyl-NH—(C=O)—, $[(R^6)_n$—$(C_1-C_6)$alkyl$]_2$—N—(C=O)—, $(R^6)_n$—$(C_1-C_6)$alkyl-O(C=O)—, $(R^6)_n$—$(C_3-C_{10})$cycloalkyl-(C=O)—, $(R^6)_n$—$(C_1-C_{10})$heterocyclyl-(C=O)—, $(R^6)_n$—$(C_6-C_{10})$aryl-(C=O)—, $(R^6)_n$—$(C_1-C_{10})$heteroaryl-(C=O)—, $(R^6)_n$—$(C_1-C_6)$alkyl-SO$_2$—, $(R^6)_n$—$(C_6-C_{10})$aryl-SO$_2$—, $(R^6)_n$—$(C_1-C_{10})$heteroaryl-SO$_2$—, H$_2$N—SO$_2$—, $(R^6)_n$—$(C_1-C_6)$alkyl-NH—SO$_2$—, and $[(R^6)_n$—$(C_1-C_6)$alkyl$]_2$N—SO$_2$—;

wherein any two $R^4$ radicals on a carbon atom of said $(C_1-C_{10})$heterocyclyl can be taken together to form an oxo group or a spiro $(C_3-C_6)$carbocyclic or $(C_1-C_6)$heterocyclic group;

each $R^5$ is independently selected from the group consisting of: $(R^8)_m$—$(C_1-C_6)$alkyl, $(R^8)_m$—$(C_1-C_{10})$heterocyclyl, $(R^8)_m$—$(C_1-C_{10})$heteroaryl, $(R^8)_m$—$(C_1-C_6)$alkyl-(C=O)—, H$_2$N(C=O)—, $(R^8)_m$—$(C_1-C_6)$alkyl-NH—(C=O)—, $[(R^8)_m$—$(C_1-C_6)$alkyl$]_2$—N—(C=O)—, $(R^8)_m$—$(C_1-C_6)$alkyl-O(C=O)—, $(R^8)_m$—$(C_3-C_{10})$cycloalkyl-(C=O)—, $(R^8)_m$—$(C_1-C_{10})$heterocyclyl-(C=O)—, $(R^8)_m$—$(C_6-C_{10})$aryl-(C=O)—$(R^8)_m$—$(C_1-C_{10})$heteroaryl-(C=O)—, and $(R^8)_m$—$(C_1-C_6)$alkyl-SO$_2$—;

wherein each of said $R^6$ is independently selected from the group consisting of: hydrogen, halogen, —CN, $(R^7)_p$—$(C_3-C_{10})$cycloalkyl, $(R^7)_p$—$(C_1-C_{10})$heterocyclyl, $(R^7)_p$—$(C_6-C_{10})$aryl, $(R^7)_p$—$(C_1-C_{10})$heteroaryl, hydroxy, $(C_1-C_6)$alkoxy, $(R^7)_p$-phenoxy, $(C_1-C_6)$alkyl-(C=O)O—; NH$_2$, $(R^7)_p$—$(C_1-C_6)$alkyl-NH—, $[(R^7)_p$—$(C_1-C_6)$alkyl$]_2$—N—, $(R^7)_p$—$(C_6-C_{10})$aryl-NH—, $(C_1-C_6)$alkyl-SO$_2$—NH—, $(C_1-C_6)$alkyl-(C=O)—, H$_2$N(C=O)—, $(C_1-C_6)$alkyl-NH—(C=O)—, $[(C_1-C_6)$alkyl$]_2$-N—(C=O)—, $(C_1-C_6)$alkyl-O(C=O)—, $(R^7)_p$—$(C_3-C_{10})$cycloalkyl-(C=O)—, $(R^7)_p$—$(C_1-C_{10})$heterocyclyl-(C=O)—, $(R^7)_p$—$(C_6-C_{10})$aryl-(C=O)—, $(R^7)_p$—$(C_1-C_{10})$heteroaryl-(C=O)—, $(C_1-C_6)$alkyl-SO$_2$—, $(R^7)_p$—$(C_6-C_{10})$aryl-SO$_2$—, $(R^7)_p$—$(C_1-C_{10})$heteroaryl-SO$_2$—, H$_2$N—SO$_2$—, $(C_1-C_6)$alkyl-NH—SO$_2$—, and $[(C_1-C_6)$alkyl$]_2$N—SO$_2$—;

wherein each of said $R^7$ is independently selected from the group consisting of: hydrogen, halogen, CF$_3$, —CN, $(C_1-C_6)$alkyl, $(C_1-C_{10})$heterocyclyl, $(C_1-C_{10})$heteroaryl, hydroxy, $(C_1-C_6)$alkoxy, $(C_1-C_6)$alkyl-O(C=O)—, $(C_1-C_6)$alkyl-SO$_2$—NH—, $(C_1-C_6)$alkyl-SO$_2$—, $(C_6-C_{10})$aryl-SO$_2$—, $(C_1-C_{10})$heteroaryl-SO$_2$—, H$_2$N—SO$_2$—, $(C_1-C_6)$alkyl-NH—SO$_2$—, and $[(C_1-C_6)$alkyl$]_2$N—SO$_2$—;

wherein each of said $R^8$ is independently selected from the group consisting of: hydrogen, halogen, —CN, $(R^9)_t$—$(C_6-C_{10})$aryl, hydroxy, $(C_1-C_6)$alkoxy, $(C_1-C_6)$alkyl-(C=O)O—; H$_2$N—(C=O)O—, $(C_1-C_6)$alkyl-NH—(C=O)O—, $((C_1-C_6)$alkyl$)_2$N—(C=O)O—, NH$_2$, $(C_1-C_6)$alkyl-NH—, $[(C_1-C_6)$alkyl$]_2$—N—, $(C_1-C_6)$alkyl)-(C=O)NH—, $(C_1-C_6)$alkyl)-NH—(C=O)NH—, $(C_1-C_6)$alkyl-SO$_2$—NH—, $(R^9)_t$—$(C_3-C_{10})$cycloalkyl-NH(C=O)—, $(R^9)_t$—$(C_1-C_{10})$heterocyclyl-NH—(C=O)—, $(R^9)_t$—$(C_6-C_{10})$aryl-NH—(C=O)—, $(R^9)_t$—$(C_1-C_{10})$heteroaryl-NH—(C=O)—, $(C_1-C_6)$alkyl-(C=O)NH—, $(C_1-C_6)$alkyl-(C=O)—, H$_2$N(C=O)—, $(C_1-C_6)$alkyl-NH—(C=O)—, $[(C_1-C_6)$alkyl$]_2$—N—(C=O)—, $(C_1-C_6)$alkyl-O(C=O)—, $(R^9)_t$—$(C_3-C_{10})$cycloalkyl-(C=O)—, $(R^9)_t$—$(C_1-C_{10})$heterocyclyl-(C=O)—, $(R^9)_t$—$(C_6-C_{10})$aryl-(C=O)—, $(R^9)_t$—$(C_1-C_{10})$heteroaryl-(C=O)—, $(C_1-C_6)$alkyl-SO$_2$—, $(R^9)_t$—$(C_6-C_{10})$aryl-SO$_2$—, $(R^9)_t$—$(C_1-C_{10})$heteroaryl-SO$_2$—, H$_2$N—SO$_2$—, $(C_1-C_6)$alkyl-NH—SO$_2$—, and $[(C_1-C_6)$alkyl$]_2$N—SO$_2$—;

wherein each of said $R^9$ is independently selected from the group consisting of: hydrogen, halogen, $(C_1-C_6)$alkyl, —CN, hydroxy, $(C_1-C_6)$alkoxy, $(C_1-C_6)$alkyl-(C=O)O—; NH$_2$, $(C_1-C_6)$alkyl-NH—, $[(C_1-C_6)$alkyl$]_2$—N—, $((C_1-C_6)$alkyl)-(C=O)NH—, $(C_1-C_6)$alkyl-(C=O)—, H$_2$N(C=O)—, $(C_1-C_6)$alkyl-NH—(C=O)— and $[(C_1-C_6)$alkyl$]_2$—N—(C=O)—;

wherein each of m, n, p, and t are independently an integer from zero to three;

wherein the molecular weight of said compound of formula I is less than 700 AMU, preferably less than 550 AMU;

or the pharmaceutically acceptable salts or solvates or prodrugs thereof.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 1 mg to 1 gram, preferably 1 mg to 250 mg, more preferably 10 mg to 100 mg.

The present invention also encompasses sustained release compositions.

The present invention also relates to processes of preparing the compounds of formula I and intermediates used in such processes.

One embodiment of the processes of the invention relates to the preparation of compounds of formula I, which may be carried out by one or more of the synthetic methods outlined in Schemes I-VIII, detailed below. The present invention also provides methods and intermediates useful in the synthesis of compounds of formula (I), and identified in Schemes I-VIII below.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-$\alpha$ inhibitors such as anti-TNF monoclonal antibodies (such as Remicade, CDP-870 and $D_2E_7$) and TNF receptor immunoglobulin molecules (such as Enbrel®), COX-2 inhibitors (such as meloxicam, celecoxib, rofecoxib, valdecoxib, paracoxib, and etoricoxib) low dose methotrexate, leflunomide; ciclesonide; hydroxychloroquine, d-penicillamine, auranofin or parenteral or oral gold.

The present invention still further relates to the combination of a compound of the invention together with a leukotriene biosynthesis inhibitor, 5-lipoxygenase (5-LO) inhibitor or 5-lipoxygenase activating protein (FLAP) antagonist selected from the group consisting of: zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonists for leukotrienes $LTB_4$, $LTC_4$, $LTD_4$, and $LTE_4$ selected from the group consisting of: the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic $H_1$ receptor antagonists including cetirizine, loratadine, desloratadine, fexofenadine, astemizole, azelastine, and chlorpheniramine.

The present invention still further relates to the combination of a compound of the invention together with a gastroprotective $H_2$ receptor antagonist.

The present invention still further relates to the combination of a compound of the invention together with an $\alpha_1$- and $\alpha_2$-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents including ipratropium bromide; tiotropium bromide; oxitropium bromide; pirenzepine; and telenzepine.

The present invention still further relates to the combination of a compound of the invention together with a $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, including prednisone, prednisolone, flunisolide, triamcinolone acetonide, beclomethasone dipropionate, budesonide, fluticasone propionate, and mometasone furoate.

The present invention still further relates to the combination of a compound of the invention together with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; (j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists selected from the group consisting of: NKP-608C; SB-233412 (talnetant); and D-4418; and (t) elastase inhibitors selected from the group consisting of: UT-77 and ZD-0892.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and farnesyl transferase inhibitors, VEGF inhibitors, COX-2 inhibitors and antimetabolites such as methotrexate antineoplastic agents, especially antimitotic drugs including the vinca alkaloids such as vinblastine and vincristine.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

DETAILED DESCRIPTION OF THE INVENTION

Compounds of the formula I may be prepared according to the following reaction schemes and discussion. Unless otherwise indicated $R^1$ through $R^9$ in the reaction schemes and discussion that follows are as defined above.

Scheme 1

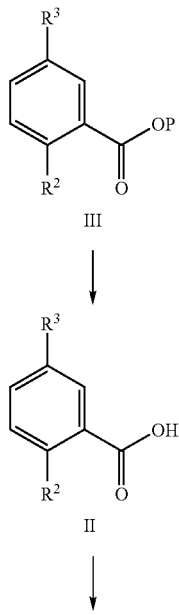

-continued

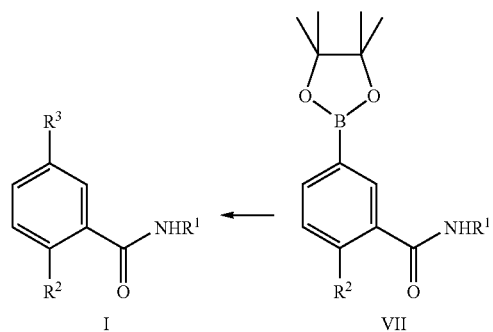

Scheme 2

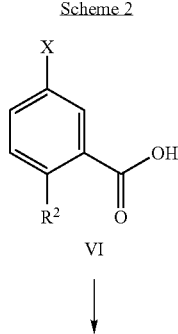

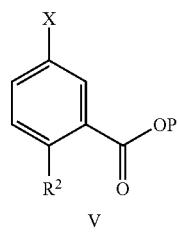

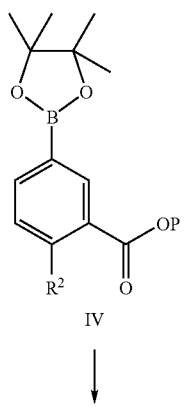

-continued
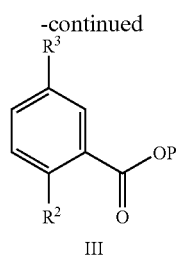
III
Scheme 3
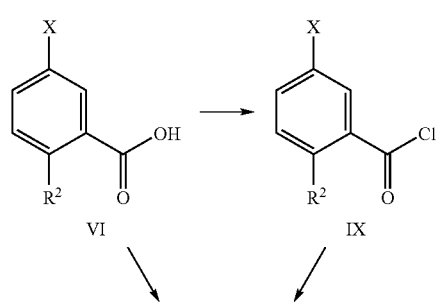
VI → IX
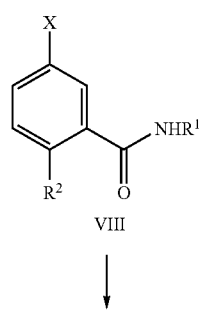
VIII
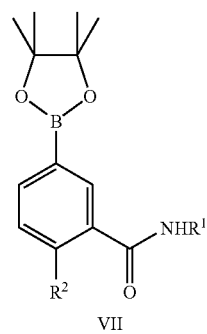
VII
Scheme 4
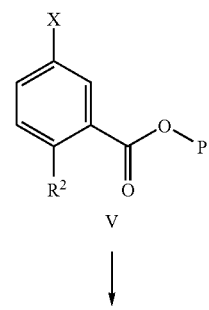
V
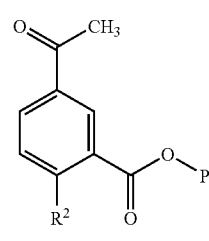
XI
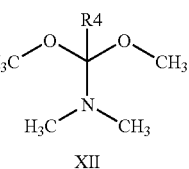
XII
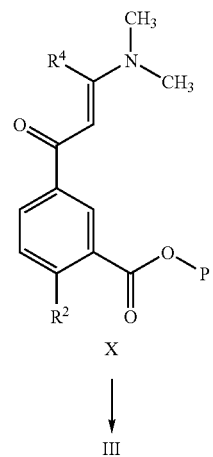
X
→ III Scheme 5
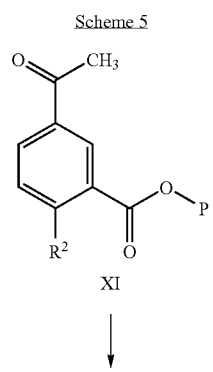
XI
↓
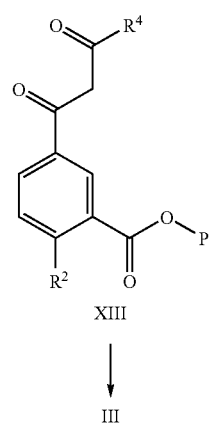
XIII
↓
III
Scheme 6
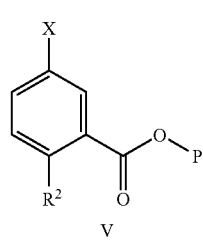
V
↓
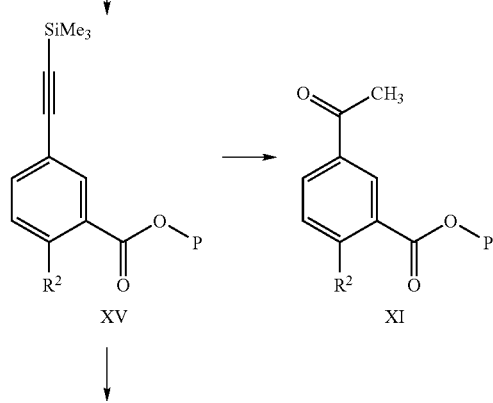
XV → XI
↓
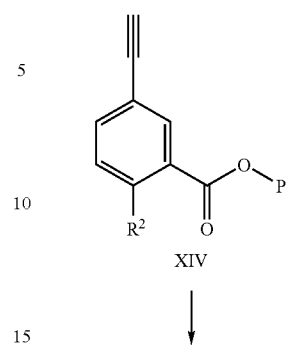
XIV
↓
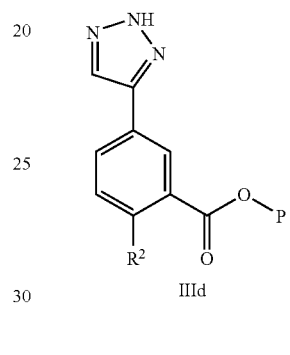
IIId
Scheme 7
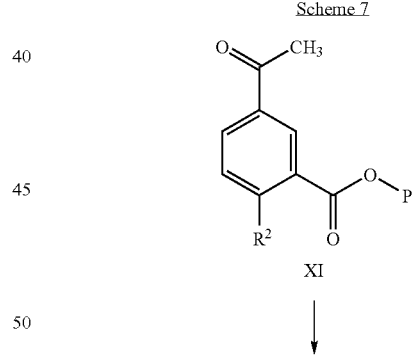
XI
↓
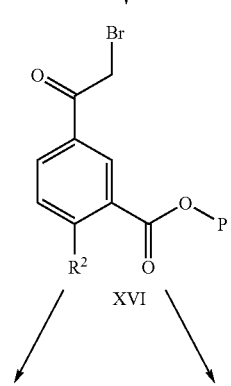
XVI
↓ ↓

-continued
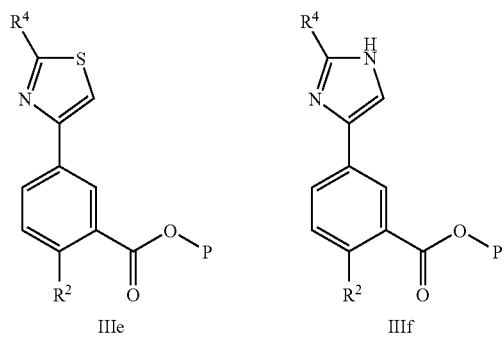
IIIe      IIIf
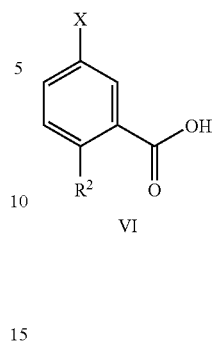
VI
Scheme 8
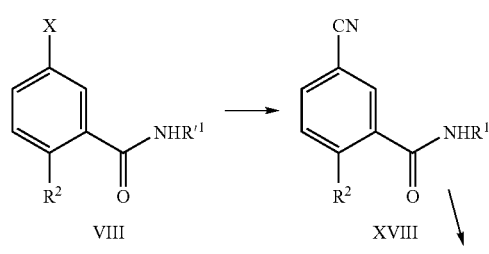
VIII      XVIII
Scheme 9
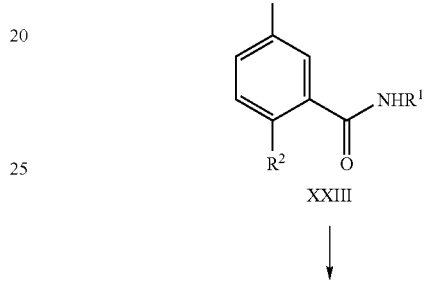
XXIII
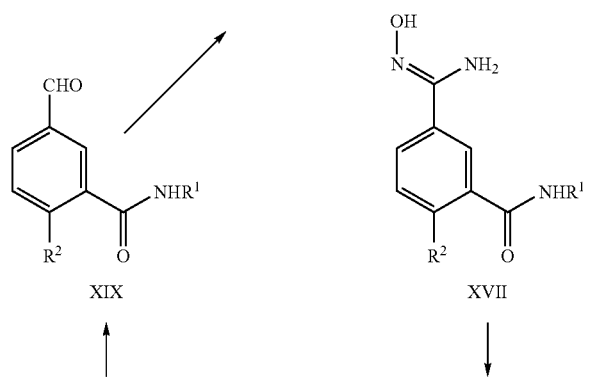
XIX      XVII
XX      Ia
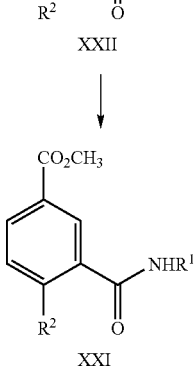
XXII
XXI
Scheme 10
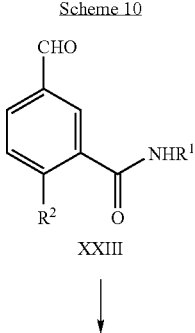
XXIII -continued
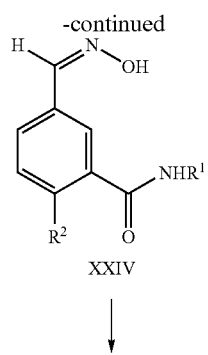
XXIV
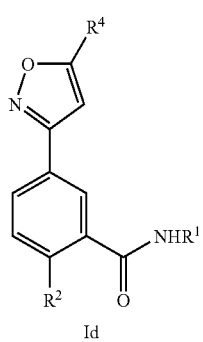
Id
Scheme 11
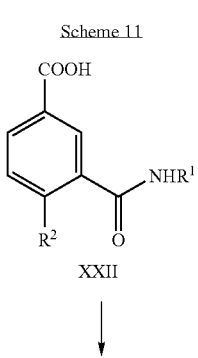
XXII
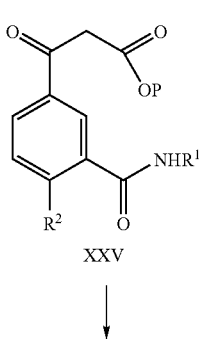
XXV
-continued
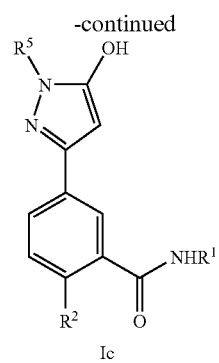
Ic
Scheme 12
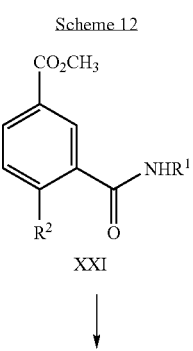
XXI
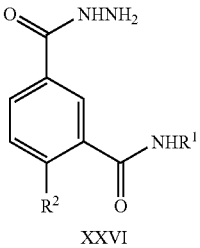
XXVI
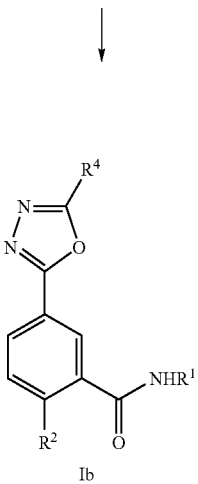
Ib Scheme 13
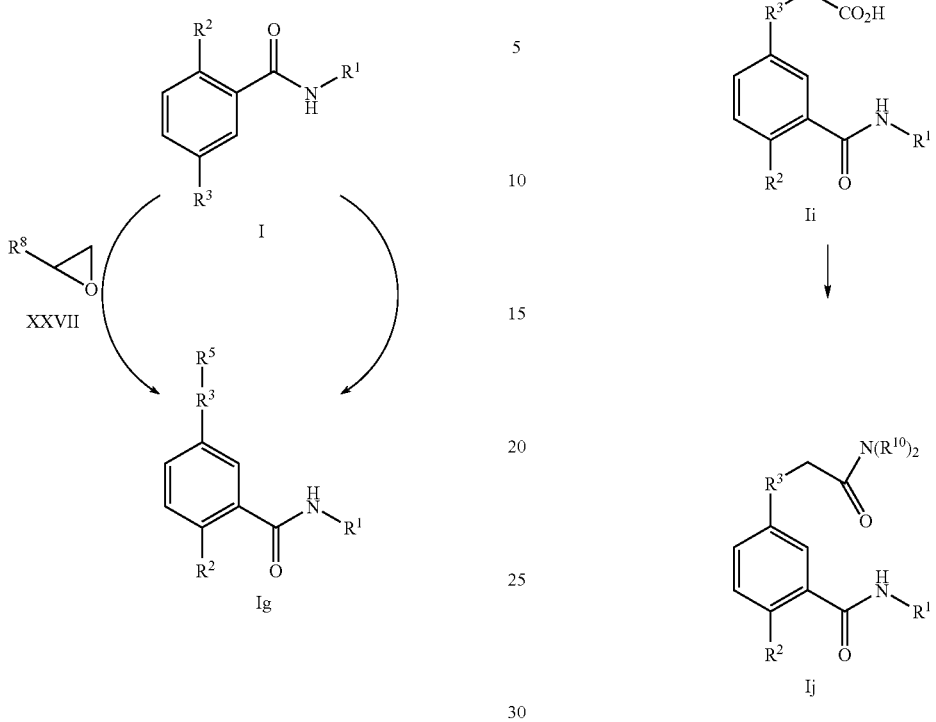
Scheme 14
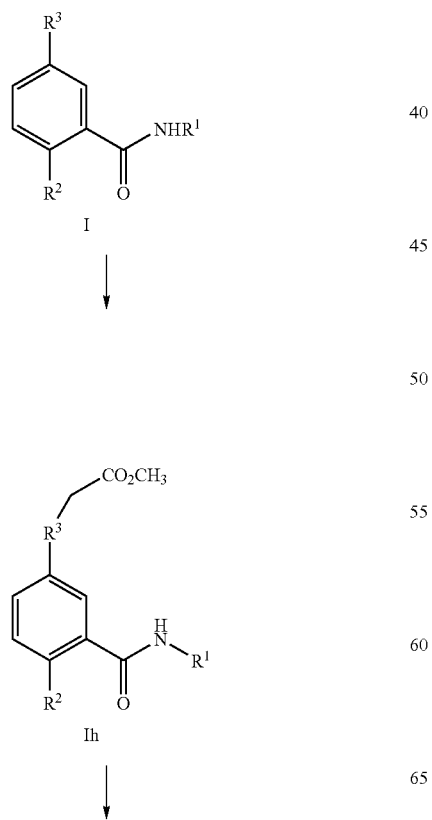
Scheme 15
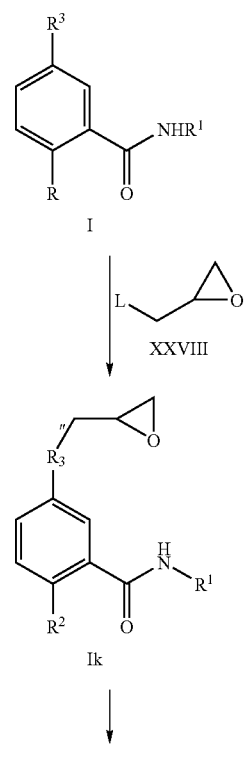

-continued

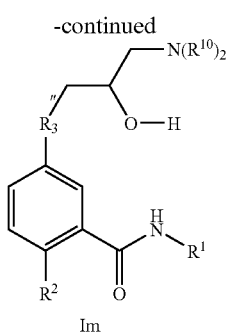

Im

Scheme 1 refers to the preparation of compounds of the formula I. Compounds of the formula I may be prepared from compounds of formula I by reaction with an amine of the formula $H_2N$—$R^1$, in the presence of a coupling reagent such as 1-[3-(dimethylamino)propyl]-3-ethylcarbodiimide (EDCI), dicyclohexylcarbodiimide (DCC), 1,1'-carbonyldiimidazole (CDI) and a base such as dimethylaminopyridine (DMAP) or triethylamine in an aprotic solvent, such as methylene chloride, dimethylformamide, or dimethylsulfoxide, preferably 1-[3-(dimethylamino)propyl]-3-ethylcarbodiimide and dimethylaminopyridine in dimethyl formamide. The aforesaid reaction may be run at a temperature from about 22° C. to about 60° C., for a period of about 1 hour to about 20 hours, preferably about 22° C. for about 18 hours.

Compounds of the formula I may be prepared by reacting a compound of the formula III, wherein P is a protecting group, with a base, such as sodium carbonate, potassium carbonate, cesium carbonate, sodium hydroxide, potassium hydroxide or lithium hydroxide, in a solvent such as methanol, ethanol, 2-propanol, tetrahydrofuran, dioxane with added water. Preferred conditions include potassium hydroxide and methanol. The aforesaid reaction may be run at a temperature from about 22° C. to about 60° C., for a period of about 1 hour to about 20 hours, preferably about 22° C. for about 18 hours.

Alternatively, a compound of the formula I may also be prepared from a compound of the formula VII by reaction with a compound of formula $R^3$—X, wherein X is a suitable leaving group, in the presence of a palladium catalyst, and a base in an aprotic solvent. Suitable leaving groups include chloro, bromo, iodo, triflate, tosylate or mesylate. Suitable palladium catalysts include 1,1'-bis(diphenylphosphino)ferrocenepalladium(II) dichloride dichloromethane, or tetrakis triphenylphosphine palladium (0). Suitable bases include potassium carbonate, cesium carbonate, triethylamine, aqueous sodium hydroxide or aqueous potassium hydroxide. Suitable solvents include methylene dimethylformamide. Preferred conditions are 1,1'-bis(diphenylphosphino) ferrocenepalladium(II) dichloride dichloromethane, aqueous sodium carbonate and dimethylfomamide. The aforesaid reaction may be run at a temperature from about 22° C. to about 100° C., for a period of about 1 hour to about 24 hours, preferably at about 80° C. for about 12 hours.

Compounds of formula III can be made according to the methods of Scheme 2 and 4-7. Compounds of formula VII can be made according to the methods of Scheme 3.

Scheme 2 refers to preparation of compounds of formula III, which are intermediates in Scheme 1 for the preparation of compounds of formula I. Referring to Scheme 2, compounds of formula III may be prepared by reacting a compound of the formula IV with a compound of formula $R^3$—X, wherein X is a suitable leaving group, in the presence of a palladium catalyst and a base in an aprotic solvent. Suitable leaving groups include chloro, bromo or iodo, preferably iodo. Suitable palladium catalysts include 1,1'-bis(diphenylphosphino)ferrocenepalladium(II) dichloride dichloromethane, or tetrakis triphenylphosphine palladium (0). Suitable bases include potassium acetate, potassium carbonate, cesium carbonate, triethylamine, aqueous sodium hydroxide or aqueous potassium hydroxide. Suitable solvents include methylene chloride and dimethylformamide. Preferred conditions include 1,1'-bis(diphenylphosphino)ferrocenepalladium(II) dichloride dichloromethane, aqueous sodium carbonate and dimethylfomamide. The aforesaid reaction may be run at a temperature from about 22° C. to about 60° C., for a period of about 1 hour to about 20 hours; preferably about 80° C. for about 18 hours.

Compounds of formula IV can be prepared by reacting a compound of the formula V, wherein X is a suitable leaving group, with bis(pinacolato)diorama in the presence of a palladium catalyst and a base in an aprotic solvent. Suitable leaving groups include bromo, iodo, chloro and triflate. Suitable palladium catalysts include 1,1'-bis(diphenylphosphino)ferrocenepalladium(II) dichloride dichloromethane or tetrakis triphenylphosphine Palladium (0). Suitable bases include potassium acetate, potassium carbonate, cesium carbonate, triethylamine, aqueous sodium hydroxide or aqueous potassium hydroxide. Suitable solvents include methylene chloride and dimethylformamide. Preferred conditions include 1,1'-bis(diphenylphosphino)ferrocenepalladium(II) dichloride dichloromethane, potassium acetate and dimethylfomamide.

A compound of the formula V can be prepared from a compound of the formula VI by reaction with methanol in the presence of an acid such as sulfuric acid or gaseous hydrochloric acid at a temperature between 22° C. and reflux for a period of 4 to 24 hours; preferably gaseous hydrochloric acid at 22° C. for 24 hours.

Compounds of formula VI are commercially available or can be made according to the methods well known to those skilled in the art.

Scheme 3 refers to the preparation of compounds of the formula VII, which are intermediates for the preparation of compounds of formula I in Scheme 1. Referring to Scheme 3, a compound of formula VII may be prepared by reacting a compound of the formula VIII, wherein X is a leaving group, with bis(pinacolato)diboron in the presence of a palladium catalyst and a base in an aprotic solvent. Suitable leaving groups include chloro, bromo, iodo or triflate, preferably bromo or iodo. Suitable palladium catalysts include 1,1'-bis(diphenylphosphino)ferrocenepalladium(II) dichloride dichloromethane or tetrakis triphenylphosphine Palladium (0). Suitable bases include potassium acetate, potassium carbonate, cesium carbonate, triethylamine, aqueous sodium hydroxide or aqueous potassium hydroxide. Suitable solvents include methylene chloride and dimethylformamide. Preferred conditions include 1,1'-bis(diphenylphosphino)ferrocenepalladium(II) dichloride dichloromethane, potassium acetate and dimethylfomamide.

Alternatively, compounds of the formula VIII may be converted directly to compounds of formula I by reaction with a borate of formula $R^3$—$B(OH)_2$ in the presence of a palladium catalyst and a base in an aprotic solvent Suitable catalysts include 1,1'-bis(diphenylphosphino)-ferrocenepalladium(II) dichloride dichloromethane, or tetrakistriphenylphosphine palladium (0); preferably tetrakistriphenylphosphine palladium (0). Suitable bases include potassium acetate, potassium carbonate, cesium carbonate, triethylamine, aqueous sodium hydroxide, aqueous sodium carbonate, aqueous potassium carbonate or aqueous potassium hydroxide. Suitable solvents include methylene chloride, ethyl acetate, toluene, dichloroethane, dimethylformamide, or dimethylsulfoxide. Preferred conditions include aqueous sodium carbonate in dimethyl formamide. The aforesaid reaction may be run at a temperature from 22° C. to 100° C., for a period of 1 hour to 20 hours, preferably 80° C. for 18 hours. Borates of the formula $R^3$—$B(OH)_2$ can be prepared by reacting a compound of formula $R^3$—X, wherein X is a leaving group as described above, with a base, and a trialkyl borate of formula $B(OR)_3$ in an aprotic solvent. Suitable bases include n-butyl lithium or isopropylmagnesium chloride; preferably isopropylmagnesium chloride. Suitable solvents include diethyl ether, tetrahydrofuran, dimethoxy ethane; preferably tetrahydrofuran. The aforementioned reaction may be run at a temperature from –78° C. to 22° C. for a period of 1 hour to 24 hours; preferably 22° C. for 18 hours. The resulting product is hydrolyzed using aqueous acid, such as hydrochloric acid, sulfuric acid, citric acid or perchloric acid; preferably hydrochloric acid. The hydrolysis reaction can be run at temperature from 22° C. to 100° C. for a period of 1 hour to 24 hours; preferably 22° C. for 4 hours.

Compounds of the formula VIII may be prepared from compounds of formula VI by reaction with a compound of formula $R^1NH_2$, in the presence of a coupling reagent such as 1-[3-(dimethylamino)propyl]-3-ethylcarbodiimide (EDCI), dicyclohexylcarbodiimide (DCC), 1,1'-carbonyldiimidazole (CDI) and a base such as dimethylaminopyridine (DMAP) or triethylamine in an aprotic solvent, such as methylene chloride, dimethylformamide, or dimethylsulfoxide; preferably 1-[3-(dimethylamino)propyl]-3-ethylcarbodiimide and dimethylaminopyridine in dimethylformamide. The aforesaid reaction may be run at a temperature from 22° C. to 60° C., for a period of 1 hour to 20 hours, preferably 22° C. for 18 hours.

Compounds of the formula VIII may also be prepared from compounds of the formula IX by reaction with a compound of formula $R^1NH_2$, in the presence of a base in an aprotic solvent. Suitable bases include dimethylaminopyridine (DMAP), triethylamine, diisopropylethylamine, aqueous sodium hydroxide or aqueous potassium hydroxide. Suitable solvents include methylene chloride, ethyl acetate, dichloroethane, dimethylformamide, or dimethylsulfoxide, preferably diisopropylethylamine and dichloroethane. The aforesaid reaction may be run at a temperature from 22° C. to 60° C., for a period of 1 hour to 24 hours, preferably at 22° C. for 3 hours.

Compounds of the formula IX may be prepared from compounds of the formula VI by reaction with a reagent capable of generating an acid chloride, such as thionyl chloride or oxalyl chloride, in the presence or absence of a polar aprotic solvent, such as ethyl acetate, methylene chloride, or dichloroethane, at a temperature of 22° C. to 80° C., for a period of 1 hour to 24 hours. Preferred conditions include thionyl chloride at 80° C. for 4 hours.

Compounds of formula VI can be prepared by methods well known to those skilled in the art.

Scheme 4 refers to an alternative preparation of compounds of the formula III, which are intermediates useful for the preparation of compounds of formula I in Schemes 1 and 2. Referring to Scheme 4, a compound of formula III may be prepared by reacting a compound of formula X with a cyclization reagent in a protic solvent, such as methanol, ethanol or iso-propanol. The aforesaid reaction may be run at a temperature from about 22° C. to about 100° C. for a period of about 1 to about 24 hours; preferably in ethanol at about 22° C. for about 16 hours.

When the cyclization reagent is a hydrazine, the compound of formula III has the formula

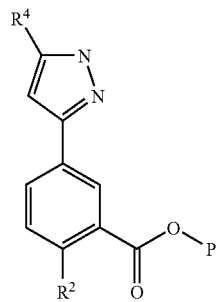

IIIa

When the cyclization reagent is a hydroxylamine, the compound of formula III has the formula

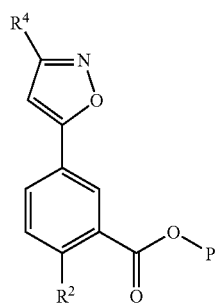

IIIb

When the cyclization reagent is an amidine, the compound of formula III has the formula

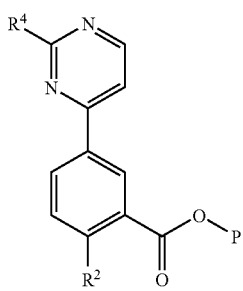

IIIc

A compound of formula X may be prepared by reacting a compound of the formula XI with a reactant of the formula XII, either in the presence or absence of a solvent, such as ethanol, methanol or tetrahydrofuran, at a temperature from 22° C. to 100° C.; preferably in the absence of solvent at 90° C. for about 4 hours.

Compounds of the formula XI may be prepared from compounds of the formula V, wherein X is a suitable leaving group, by reaction with acetic anhydride, a palladium catalyst, lithium chloride and a base in an aprotic solvent. Suitable leaving groups include bromo, iodo, chloro or triflate; preferably iodo. Suitable palladium catalysts include 1,1'-bis (diphenylphosphino)-ferrocenepalladium(II) dichloride dichloromethane, tetrakis triphenylphosphine palladium (0), or tris(dibenzylideneacetone)dipalladium(0); preferably, tris (dibenzylideneacetone)dipalladium(0). Suitable bases include dimethylaminopyridine (DMAP), triethylamine and diisopropylethylamine. Suitable solvents include methylene chloride, ethyl acetate, dichloroethane, dimethylformamide, or dimethylsulfoxide, preferably diisopropylethylamine and dimethylformamide. The aforesaid reaction may be run at a temperature from about 22° C. to about 100° C., for a period of about 1 hour to about 24 hours, preferably at about 100° C. for about 12 hours.

Compounds of formula V may be prepared according to the methods of Scheme 2. Compounds of the formula XII are commercially available or can be made by methods well known to those skilled in the art.

Scheme 5 refers to an alternate preparation of compounds of the formula III (i.e. IIIa, IIIb, and IIIc), which are intermediates useful for the preparation of compounds of formula I in Schemes 1 and 2. Referring to Scheme 5, a compound of formula III (i.e. IIIa, IIIb, and IIIc) may be prepared by reacting a compound of formula XIII with a cyclization reagent in a protic solvent, such as methanol, ethanol or iso-propanol. Suitable cyslization reagents are as described above in Scheme 4 for the conversion of compounds of formula X into compounds of the formula IIIa, IIIb, and IIIc, respectively. The aforesaid reaction may be run at a temperature from about 22° C. to about 100° C. for a period of 1 hour to about 24 hours; preferably in ethanol at about 22° C. for about 16 hours.

Compounds of formula XIII may be prepared by reacting a compound of formula XI with a compound of formula $R^4$—(C=O)—X, wherein X is a leaving group, with a base in an aprotic solvent Suitable leaving groups include chloro, bromo or alkoxy, preferably chloro. Suitable bases include potassium tertiary butoxide, dimethylaminopyridine (DMAP), triethylamine and diisopropylethylamine. Suitable solvents include ethylether, tetrahydrofuran, toluene or dimethylformamide; preferably toluene. The aforementioned reaction may be run at temperature 0° C. to 80° C. for about 1 to about 24 hours, preferably about 0° C. to about 22° C. for about 2 hours.

Compounds of formula XI can be prepared according to the methods of Scheme 4.

Scheme 6 refers to an alternative preparation of compounds of formula IIId, which are compounds of formula III, wherein $R^3$ is triazolyl. Compounds of formula IIId are useful intermediates in the preparation of compounds of formula I in Schemes 1 and 2. Referring to Scheme 6, a compound of formula IIId can be prepared by reacting a compound of formula XIV with trimethylsilyl azide in a protic solvent such as methanol, ethanol or n-butyl alcohol; preferably n-butylalcohol. The aforesaid reaction may be run at a temperature from about 22° C. to about 150° C., for a period of about 1 hour to about 144 hours, preferably about 125° C. for about 120 hours.

A compound of formula XIV can be prepared by reacting a compound of the formula XV with 96%-98% formic acid. The aforementioned reaction may be run at temperature from about 22° C. to about 120° C. for a period of about 1 hour to about 120 hours; preferably with 98% formic acid at about 22° C. for about 12 hours.

A compound of formula XV may be prepared by reacting a compound of formula V, wherein X is a suitable leaving group, with an acetylene of the formula $(CH_3)_3Si$—C≡C—H, and a base in the presence or absence of an aprotic solvent Suitable leaving groups include bromo, iodo, chloro or triflate, preferably iodo. Suitable bases include triethylamine and diisopropylethylamine. Suitable solvents include methylene chloride, tetrahydrofuran, dimthylformamide or dioxane, preferably in the absence of a solvent. The aforesaid reaction may be run at a temperature from about 22° C. to about 100° C., for a period of 1 hour to 20 hours, preferably at 100° C. for 18 hours.

Compounds of the formula XV may also be used in an alternate preparation to form compounds of formula XI, which are intermediates for the preparation of compounds of formula III in Scheme 4. Compounds of formula XV may be reacted with 96%-98% formic acid to form a compound of formula XI. The aforementioned reaction may be run at temperature from about 22° C. to about 120° C. for a period of about 1 hour to about 120 hours, preferably with 98% formic acid at about 100° C. for about 120 hours.

Compounds of the formula V may be prepared according to the methods of Scheme 2.

Scheme 7 refers to an alternate preparation of compounds of formulas IIIe and IIIf. Compounds of the formula If may be prepared from compounds of formula XVI by reaction with a compound of the formula $R^4$—(C=NH)—$NH_2$ in an aprotic solvent such as dimethylsulfoxide, tetrahydrofuran, dimethlyformamide or toluene, at a temperature ranging from about 0° C. to about 100° C. for a period of about 15 minutes to about 18 hours. The preferred conditions are tetrahydrofuran at about 60° C. for about 1 hour.

Compounds of the formula IIIe may be prepared from compounds of the formula XVI by reaction with a compound of the formula $R^4$—(C=S)—$NH_2$ in a protic or aprotic solvent, such as dimethylsulfoxide, ethanol, tetrahydrofuran, dimethylformamide or toluene, at a temperature ranging from about 0° C. to about 100° C. for a period of about 15 minutes to about 18 hours. The preferred conditions are ethanol at about 50° C. for about 0.5 hour.

Compounds of the formula XVI may be prepared from compounds of the formula XI by reaction with bromine under various conditions known to those skilled in the art (H. O. House, "Modern Synthetic Reactions," W. A. Benjamin, Inc., Menlo Park, Calif. (1972), pp 459-478).

Compounds of formula XI may be made by the methods of Schemes 4 and 6.

Scheme 8 refers to an alternate preparation of compounds of formula Ia. Compounds of the formula Ia may be prepared from compounds of formula XVII by reaction with a compound of the formula $R^4(C=O)Cl$ or $(R^4—(C=O))_2O$ in the presence or absence of an aprotic solvent such as dimethylsulfoxide, tetrahydrofuran, dimethlyformamide or methylene chloride, at a temperature ranging from about 20° C. to about 150° C. for a period of about 1 hour to about 18 hours. The preferred conditions are neat at about 120° C. for about 2 hours.

Compounds of the formula XVII can be prepared from compounds of the formula XVIII by reaction with hydroxylamine in a protic solvent, such as methanol or ethanol, at a temperature ranging from about 20° C. to about 100° C. for a period of about 1 hour to about 24 hours. The preferred conditions are methanol at about 60° C. for about 18 hours.

Compounds of formula XVIII can be prepared from compounds of the formula VIII by reaction with a cyanide reagent in the presence or absence of a palladium catalyst in an aprotic solvent at a temperature ranging from about 50° C. to about 200° C. for a period of about 1 hour to about 48 hours (Tetrahedron Letters 40 (1999) 8193-8195; 41 (2000) 3271-3273; 42 (2001) 6707-6710; 43 (2002) 387-389). Suitable cyanide reagents include zinc cyanide, copper cyanide, sodium cyanide and potassium cyanide. Suitable palladium catalysts include 1,1'-bis(diphenylphosphino)ferrocenepalladium(II) dichloride, dichloromethane, or tetrakis triphenylphosphine Palladium (0). Suitable solvents include dimethylformamide, dimethylacetamide, N-methylpyrrolidinone and toluene.

Compounds of the formula XVIII may also be prepared from compounds of the formula XIX by reaction with hydroxylamine hydrochloride and derivatives thereof under the conditions known to those skilled in the art (March, J. Advanced Organic Chemistry; John Wiley & Sons: New York, 1985; pp. 806-807).

Compounds of the formula XIX can be prepared from compounds of the formula XX by reaction with a reagent of the formula $NH_2$—$R^1$, in the presence of a coupling reagent and a base, such as dimethylaminopyridine (DMAP) or triethylamine, in an aprotic solvent Suitable coupling agents include 1-[3-(dimethylamino)propyl]-3-ethylcarbodiimide (EDCI), dicyclohexylcarbodiimide (DCC), 1,1'-carbonyldiimidazole (CDI), polymer bound carbodiimide and 1-hydroxy benzotriazole. Suitable solvents include methylene chloride, dimethylformamide, or dimethylsulfoxide. Preferred conditions include polymer bound carbodiimide and 1-hydroxy benzotriazole in dimethyl formamide. The aforesaid reaction may be run at a temperature from about 22° C. to about 60° C., for a period of about 1 hour to about 20 hours, preferably about 22° C. for about 18 hours.

Compounds of the formula XX can be prepared from compounds of the formula VI by reaction with a base, such as methyl lithium, n-butyllithium or tert-butyllithium, in an aprotic solvent, such as ethyl ether, tetrahyrofuran or hexane, at a temperature ranging from about −80° C. to about 25° C. for a period of about 10 minutes to about 1 hour, followed by reaction with dimethylformamide in the same pot for a period of about 0.5 hours to about 3 hours. The preferred conditions are methyl lithium (1 equivalent) followed by tert-butyllithium (1 equivalent) in tetrahydrofuran at about −78° C. for about 10 minutes, followed by reaction with dimethylformamide for about 30 minutes.

Compounds of the formula VI are commercially known or may be prepared according to the methods well known to those skilled in the art.

Scheme 9 refers to the preparation of compounds of the formulae XXI and XXII, which are intermediates in the preparation of compounds of formula I in Schemes 10-12. Referring to Scheme 9, a compound of the formula XXI can be prepared from a compound of the formula XXII by various methods known to those skilled in the art [R. C. Larock, "Comprehensive Organic Transformations. A Guide to Functional Group Preparations," VCH Publishers, Inc., New York, N.Y. (1989), pp. 966-972].

Compounds of the formula XXII can be prepared from compounds of the formula XXIII also by various methods known to those skilled in the art (R. C. Larock, "Comprehensive Organic Transformations. A Guide to Functional Group Preparations," VCH Publishers, Inc., New York, N.Y. (1989), pp. 838-841).

Compounds of formula XXIII are commercially available or can be made by methods well known to those skilled in the art.

Scheme 10 refers to an alternative preparation of compounds of the formula Id. Compounds of the formula Id can be prepared from compounds of the formula XXIV by reaction with a reagent of the formula HC≡C—$R^4$, sodium hypochlorite and a base, such as triethylamine or diethylisopropyl amine, in a solvent, such as dichloromethane or dichloroethane, at a temperature ranging from 0° C. to 60° C. for a period of 3 hours to 72 hours. The preferred conditions are triethylamine, dichloromethane, 22° C. for 20 hours.

Compounds of the formula XXIV may be prepared from compounds of the formula XXIII by reaction with hydroxylamine or hydroxylamine hydrochloride under the conditions known to those skilled in the art (March, J. Advanced Organic Chemistry; John Wiley & Sons: New York, 1985; pp. 805-806).

Scheme 11 refers to an alternative preparation of compounds of the formula Ic. Compounds of the formula Ic can be prepared from compounds of the formula XXV by reaction with a reagent of the formula $NH_2NHR^5$ in the presence or absence of a solvent such as methanol, ethanol, tetrahydrofuran or dimethylformamide, at a temperature ranging from 22° C. to 150° C. for a period of 1 hour to 24 hours. The preferred conditions are ethanol, 80° C. for 12 hours.

Compounds of the formula XXV can be prepared from compounds of the formula XXII by reaction with carbonyldiimidazole in a solvent including, but not limited to tetrahydrofuran, ether and dichloromethane at a temperature ranging from 0° C. to 60° C. for a period of 1 hour to 24 hours, followed by reaction with the magnesium salt of monomethyl malonate at a temperature ranging from 0° C. to 60° C. for a period of 1 hour to 24 hours. The preferred conditions are carbonyldiimidazole in tetrahydrofuran at 22° C. for 6 hours, followed by reaction with the magnesium salt of monomethyl malonate at 22° C. for 12 hours (D. W. Brooks, L. D. Lu and S. Masamune *Angew. Chem. Int. Ed. Eng.* 18 (1979) p. 72).

Scheme 12 refers to an alternate preparation of compounds of formula Ib. Compounds of the formula Ib may be prepared from compounds of the formula XXVI by reaction with a reagent of the formula $R^4C(—OR)_3$ in the presence or absence of a solvent, such as dimethylacetamide, dimethylformamide or xylene, at a temperature ranging from 50° C. to 200° C. for a period of 1 hour to 12 hours. The preferred conditions are no solvent, 140° C. for 2 hours.

Compounds of the formula XXVI may be prepared from compounds of the formula XXI by reaction with hydrazine or hydrazine hydrate in the presence or absence of a solvent, such as methanol or ethanol, at a temperature ranging from 50° C. to 150° C. for a period of 1 hour to 24 hours. The preferred conditions are no solvent, 120° C. for 2 hours.

Scheme 13 refers to an alternate preparation of compounds of the formula Ig. Compounds of the formula Ig may be prepared from other compounds of formula I (wherein $R^5$ is H) by reaction with a compound of the formula L-$R^5$, in the presence of a base, wherein L is a suitable leaving group, such as chloro, bromo, iodo, tosylate or mesylate. Suitable bases include triethylamine, polymer supported 2-tert-butylimino-2-diethylamino-1,3-dimethylperhydro-1,3,2-diazaphosphorine (BEMP), cesium carbonate, potassium carbonate, and sodium hydride; cesium carbonate is preferred. The aforesaid reaction can be performed at temperatures ranging from 0° C. to 100° C. in the presence of a polar solvent including, but not limited to dimethylsulfoxide, dimethylformamide, equal amounts of dimethylsulfoxide and acetone, or equal amounts of dimethylformamide and acetone, generally for a period of 2 hours to 72 hours, where the preferred conditions are dimethylsulfoxide at 80° C. for 18 hours.

Compounds of the formula Ig may also be prepared from other compounds of the formula I by reaction of an appropriately substituted epoxide of the formula XXVII either neat or in the presence of a polar solvent including but not limited to dimethylformamide, dimethylsulfoxide, and tetrahydrofuran. The aforesaid reaction can be performed at temperatures ranging from 0° C. to 100° C. for a period of 2 to 72 hours, wherein the preferred conditions are dimethylforamide at 60° C. for 16 hours.

Scheme 14 refers to alternative preparations of compounds of the formulae Ih, Ii and Ij. Compounds of the formula Ij may be prepared from compounds of formula I by reaction with a compound of formula $HN(R^{10})_2$, wherein $R^{10}$ is as described above for amide substituents in $R^8$, in the presence of a coupling reagent and a base, such as dimethylaminopyridine (DMAP) or triethylamine, in an aprotic solvent. Suitable coupling agents include 1-[3-(dimethylamino)propyl]-3-ethylcarbodiimide (EDCI), dicyclohexylcarbodiimide (DCC), 1,1'-carbonyldiimidazole (CDI), polymer bound carbodiimide and 1-hydroxy benzotriazole. Suitable solvents include methylene chloride, dimethylformamide, or dimethylsulfoxide. Preferred conditions include polymer bound carbodiimide and 1-hydroxy benzotriazole in dimethyl formamide. The aforesaid reaction may be run at a temperature from about 22° C. to about 60° C., for a period of about 1 hour to about 20 hours, preferably about 22° C. for about 18 hours.

Compounds of the formula Ii may be prepared by reacting a compound of the formula Ih and a base, such as sodium carbonate, potassium carbonate, cesium carbonate, sodium hydroxide, potassium hydroxide or lithium hydroxide, in a solvent, such as methanol, ethanol, 2-propanol, tetrahydrofuran, dioxane with added water, preferably potassium hydroxide and methanol. The aforesaid reaction may be run at a temperature from 22° C. to 60° C., for a period of 1 hour to 20 hours, preferably 22° C. for 18 hours.

Compounds of the formula Ih may be prepared from other compounds of formula I by reaction with a compound of the formula L-$(CH_2)_n$—$CO_2P$ in the presence of base, wherein L is a suitable leaving group, such as chloro, bromo, iodo tosylate or mesylate; and P is a suitable protecting group such as alkyl. Suitable bases include triethylamine, polymer supported BEMP, cesium carbonate, potassium carbonate, and sodium hydride; polymer supported BEMP is preferred. The aforesaid reaction can be performed at temperatures ranging from 0° C. to 100° C. in the presence of a polar solvent; such as acetonitrile, varying combinations of acetonitrile and dimethylformamide, dimethylsulfoxide, dimethylformamide, equal amounts of dimethylsulfoxide and acetone, or equal amounts of dimethylformamide and acetone, generally for a period of 2 hours to 72 hours, where the preferred conditions are a 3:2 ratio of acetonitrile and dimethylformamide at 22° C. for 4 hours.

Scheme 15 refers to the preparation of compounds of the formulae Ik and Im. Compounds of the formula Im can be prepared from compounds of formula Ik by reacting with a compound of formula $HN(R^{10})_2$, wherein $R^{10}$ is as described above for amine substituents in $R^8$, either neat or in the presence of a polar solvent including, but not limited to methyl alcohol, ethyl alcohol, dimethylformamide, dimethylsulfoxide, and tetrahydrofuran. The aforesaid reaction can be performed at temperatures ranging from 0° C. to 100° C. for a period of 2 to 72 hours, where the preferred conditions are methanol at 65° C. for 16 hours.

Compounds of the formula Ik can be prepared from other compounds of formula I by reaction with a compound of the formula XXVIII in the presence of base, wherein L is a suitable leaving group, such as chloro, bromo, iodo tosylate, nosylate or mesylate. Suitable bases include, but are not limited to, triethylamine, polymer supported BEMP, cesium carbonate, potassium carbonate, and sodium hydride; polymer supported BEMP is preferred. The aforesaid reaction can be performed at temperatures ranging from 0° C. to 100° C. in the presence of a polar solvent, such as acetonitrile, varying combinations of acetonitrile and dimethylformamide, dimethylsulfoxide, dimethylformamide, equal amounts of dimethylsulfoxide and acetone, or equal amounts of dimethylformamide and acetone, generally for a period of 2 hours to 72 hours, wherein the preferred conditions are a 3:2 ratio of acetonitrile and dimethylformamide at 80° C. for 8 hours.

The activity of the compounds of the invention for the various disorders described above can be determined according to one or more of the following assays. All of the compounds of the invention that were tested had an $IC_{50}$ of less than 10 µM in the in vitro assay described below.

Preferably, the compounds of the invention have an $IC_{50}$ in the in vitro assays described below of less than 100 nM, more preferably less than 50 nM, and most preferably less than 10 nM. Still further, the compounds of the invention preferably have an $IC_{50}$ in the range of 0.01 nM-100 nM, more preferably between 0.05 nM-50 nM, and most preferably between 0.10 nM-10 nM.

Pharmacological Analysis

Certain compounds such as benzoylbenzoyl adenosine triphosphate (bbATP) are known to be agonists of the $P2X_7$ receptor, effecting the formation of pores in the plasma membrane (Drug Development Research (1996), 37 (3), p. 126). Consequently, when the receptor is activated using bbATP in the presence of ethidium bromide (a fluorescent DNA probe), an increase in the fluorescence of intracellular DNA-bound ethidium bromide is observed. Alternatively, the propidium dye YOPRO-1 can be substituted for ethidium bromide so as to detect uptake of the dye. The increase in fluorescence can be used as a measure of $P2X_7$ receptor activation and therefore to quantify the effect of a compound on the $P2X_7$ receptor.

In this manner, the compounds of the invention can be tested for antagonist activity at the $P2X_7$ receptor. 96-Well flat bottomed microtitre plates are filled with 250 µl of test solution comprising 200 µl of a suspension of THP-1 cells (2.5× $10^6$ cells/ml, more preferably prestimulated as described in the literature with a combination of LPS and TNF to promote receptor expression) containing $10^{-4}$M ethidium bromide, 25 µl of a high potassium, low sodium buffer solution (10 mM Hepes, 150 mM KCl, 5 mM D-glucose and 1.0% FBS at pH 7.5) containing $10^{-5}$M bbATP, and 25 µl of the high potassium buffer solution containing $3\times10^{-5}$M test compound (more preferably $5\times10^{-4}$M, more preferably $1\times10^{-4}$M more preferably $1\times10^{-3}$M). The plate is covered with a plastic sheet and incubated at 37° C. for one hour. The plate is then read in a Perkin-Elmer fluorescent plate reader, excitation 520 nm, emission 595 nm, slit widths: Ex 15 nm, Em 20 nm. For the purposes of comparison, bbATP (a $P2X_7$ receptor agonist) and pyridoxal 5-phosphate (a $P2X_7$ receptor antagonist) can be used separately in the test as controls. From the readings obtained, a $pIC_{50}$ figure can be calculated for each test compound, this figure being the negative logarithm of the concentration of test compound necessary to reduce the bbATP agonist activity by 50%.

In like manner, the compounds of the invention can be tested for antagonist activity at the $P2X_7$ receptor using the cytokine IL-1β as the readout. Blood collected from normal volunteers in the presence of heparin is fractionated using lymphocyte separation medium obtained from Organon Technica (Westchester, Pa.). The region of the resulting gradient containing banded mononuclear cells is harvested, diluted with 10 ml of Maintenance Medium (RPMI 1640, 5% FBS, 25 mM Hepes, pH 7.2, 1% penicillin/streptomycin), and cells are collected by centrifugation. The resulting cell pellet was suspended in 10 ml of Maintenance Medium and a cell count was performed. In an average experiment, $2 \times 10^5$ mononuclear cells are seeded into each well of 96-well plates in a total volume of 0.1 ml. Monocytes are allowed to adhere for 2 hours, after which the supernatants are discarded and the attached cells are rinsed twice and then incubated in Maintenance Medium overnight at 37° C. in a 5% $CO_2$ environment.

The cultured monocytes can be activated with 10 ng/ml LPS (*E. coli* serotype 055:B5; Sigma Chemicals, St. Louis, Mo.). Following a 2-hour incubation, the activation medium is removed, the cells are rinsed twice with 0.1 ml of Chase Medium (RPMI 1640, 1% FBS, 20 mM Hepes, 5 mM $NaHCO_3$, pH 6.9), and then 0.1 ml of Chase Medium containing a test agent is added and the plate is incubated for 30 minutes; each test agent concentration can be evaluated in triplicate wells. ATP then is introduced (from a 100 mM stock solution, pH 7) to achieve a final concentration of 2 mM and the plate is incubated at 37° C. for an additional 3 hours. Media were harvested and clarified by centrifugation, and their IL-1□ content was determined by ELISA (R&D Systems; Minneapolis, Minn.).

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous), topical or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution, dry powder formulation or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, heptafluoroalkanes, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (inflammation) is 0.1 to 200 mg of the active ingredient per unit dose which could be administered, for example, 1 to 4 times per day.

The compound of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Aerosol formulations for treatment of the conditions referred to above in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

Aerosol combination formulations for treatment of the conditions referred to above (e.g., adult respiratory distress syndrome) in the average adult human are preferably arranged so that each metered dose or "puff" of aerosol contains from about 1 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

Aerosol formulations for treatment of the conditions referred to above (e.g., adult respiratory distress syndrome) in the average adult human are preferably arranged so that each metered dose or "puff" of aerosol contains from about 20 μg to 1000 μg of the compound of the invention. The overall daily dose with an aerosol will be within the range 100 μg to 10 mg of the P2X$_7$ receptor inhibitor. Administration may be several times daily, for example 2, 3, 4 or 8 times, giving for example, 1, 2 or 3 doses each time.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The following Examples illustrate the preparation of the compounds of the present invention. The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. All patents, applications, publications, test methods, literature, and other materials cited herein are hereby incorporated herein by reference in their entireties. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonitrile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 AMU to 1100 AMU. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32-63 mm silica gel and executed under nitrogen pressure (flash chromatography) conditions. Room or ambient temperature refers to 20-25° C. All non-aqueous reactions were run under a nitrogen atmosphere for convenience and to maximize yields. Concentration at reduced pressure means that a rotary evaporator was used.

One of ordinary skill in the art will appreciate that in some cases protecting groups may be required during preparation. After the target molecule is made, the protecting group can be removed by methods well known to those of ordinary skill in the art, such as described in Greene and Wuts, "Protective Groups in Organic Synthesis" (3rd Ed, John Wiley & Sons 1999).

EXAMPLE 1

2-Chloro-5-(6-methyl-pyridin-3-yl)-N-(1-p-tolyl-cyclohexylmethyl)-benzamide

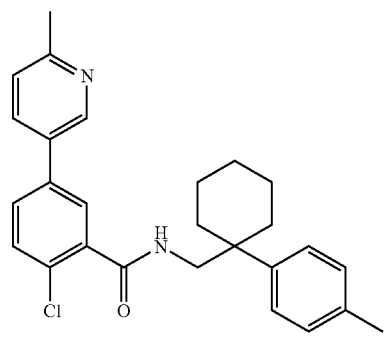

2-Chloro-5-iodo-benzoic acid methyl ester

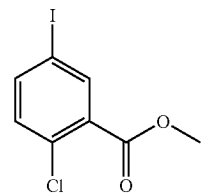

A solution of 2-chloro-5-iodo-benzoic acid (25.63 g, 90 mmol) in methanol (500 mL) saturated with HCL gas was stirred at room temperature for 48 h. The reaction mixture was concentrated in vacuo, diluted with 1:1 ethyl acetate/Diethyl ether and washed with saturated aqueous sodium bicarbonate and brine. The organic layer was dried over sodium sulfate, filtered and concentrated in vacuo to afford the title compound (25.0 g).

2-Chloro-5-(4,4,5,5-tetramethyl-[1,3,2]dioxaborolan-2-yl)-benzoic acid methyl ester

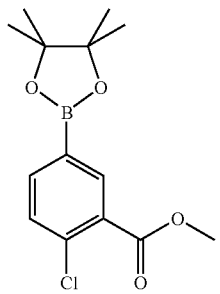

A mixture of 2-chloro-5-iodo-benzoic acid methyl ester (3.0 g, 10.17 mmol), bis(pinacolato)diborane (4.12 g, 16.27 mmol), [1,1'-bis(diphenylphosphino)ferrocene] dichloropalladium (II) dichloromethane (0.37 g, 0.46 mmol) and potassium acetate (4.48 g, 45.77 mmol) in N,N-dimethylformamide (50 mL) was heated at 90° C. for 7 h, then at room temperature for a further 16 h. The mixture was diluted with 2:1 ethyl acetate-diethyl ether (250 mL) and filtered. The filtrate was washed with water and brine, dried over sodium sulfate and concentrated in vacuo. The residue was purified by flash column chromatography eluting with diethyl ether to afford the title compound as a dark oil (2.5 g)

2-Chloro-5-(6-methyl-pyridin-3-yl)-benzoic acid methyl ester

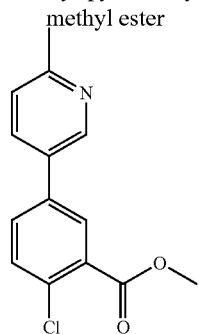

To a mixture of 2-chloro-5-(4,4,5,5-tetramethyl-[1,3,2]dioxaborolan-2-yl)-benzoic acid methyl ester (628 mg, 2.12 mmol), cesium carbonate (1.38 g, 4.25 mmol), tetrakis(triphenylphosphine) palladium (62 mg, 0.08 mmol) and molecular sieves (2 g, 4 Å) in 1,4-dioxane (10 mL) was added 2-chloro-5-methylpyridine (226 mg, 1.77 mmol). The mixture was stirred for a few minutes at room temperature then warmed to 80° C. for 4 h. A further portion of tetrakis(triphenylphosphine) palladium (120 mg, 0.10 mmol) was added and the resulting mixture was stirred at 80° C. for 16 h. A second portion of 2-chloro-5-methylpyridine (117 mg, 0.66 mmol) was added. The resulting mixture was stirred at 80° C. for a further 5 h. The reaction mixture was diluted with acetonitrile (30 mL) and filtered through a pad of celite. The filtrate was concentrated in vacuo and purified by flash column chromatography (gradient 5-100% ethyl acetate-hexane) to afford the title compound (146 mg).

2-Chloro-5-(6-methyl-pyridin-3-yl)-benzoic acid

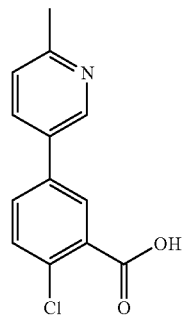

A solution of 2-chloro-5-(6-methyl-pyridin-3-yl)-benzoic acid methyl ester (146 mg, 0.56 mmol) in methanolic potassium hydroxide (2.24 mL, 1M) was stirred at 80° C. for 16 h. The reaction mixture was acidified (pH 3) with 1N HCl and concentrated in vacuo. The residue was shaken thoroughly with methanol and filtered. The filtrate was concentrated in vacuo to afford the title compound (170 mg).

2-Chloro-5-(6-methyl-pyridin-3-yl)-N-(1-p-tolyl-cyclohexylmethyl)-benzamide

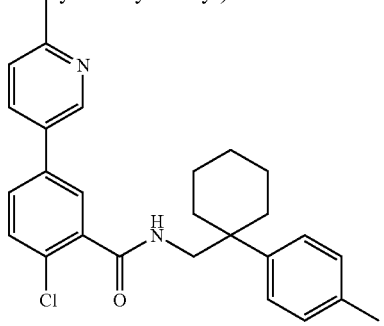

To a solution of 2-chloro-5-(6-methyl-pyridin-3-yl)-benzoic acid (73 mg, 0.29 mmol) in N,N-dimethylformamide (4 mL) was added sequentially, stirring at room temperature for 10 minutes after each addition, 1-hydroxybenzotriazole (48 mg, 0.35 mmol), 1-(3-dimethylaminopropyl)-3-ethylcarbodiimide hydrochloride (62 mg, 0.32 mmol), C-(1-p-tolyl-cyclohexyl)-methylamine (60 mg, 0.29 mmol) and triethylamine (31 mg, 0.31 mmol). The mixture was stirred at room temperature for 3 h. The reaction mixture was diluted with water and extracted with ethyl acetate. The combined organic extracts were washed with brine, dried over sodium sulfate, filtered and concentrated in vacuo. The residue was purified by reverse phase chromatography to afford the title compound (35 mg). LCMS (m/z) 433.2 M+1.

The following compounds can be made according to the method of Example 1:

| EXAMPLES | STRUCTURE | NAME | LCMS (m/z) M + 1. |
|---|---|---|---|
| 2 | 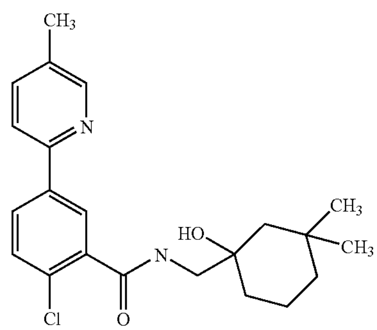 | 2-Chloro-N-(1-hydroxy-3,3-dimethyl-cyclohexylmethyl)-5-(5-methyl-pyridin-2-yl)-benzamide | 387.6 |
| 3 | 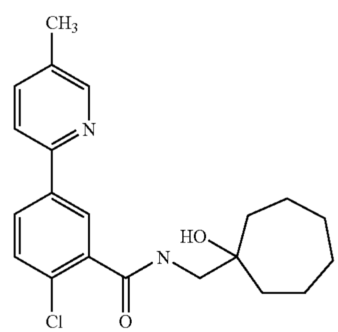 | 2-Chloro-N-(1-hydroxy-cycloheptylmethyl)-5-(5-methyl-pyridin-2-yl)-benzamide | 373.5 |
| 4 | 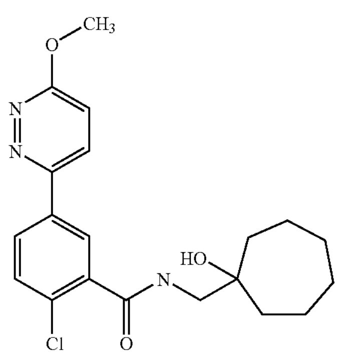 | 2-Chloro-N-(1-hydroxy-cycloheptylmethyl)-5-(6-methoxy-pyridazin-3-yl)-benzamide | 390.3 |
| 5 | 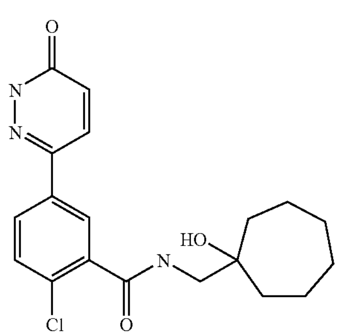 | 2-Chloro-N-(1-hydroxy-cycloheptylmethyl)-5-(6-oxo-1,6-dihydro-pyridazin-3-yl)-benzamide | 376.3 |

-continued

| EXAMPLES | STRUCTURE | NAME | LCMS (m/z) M + 1. |
|---|---|---|---|
| 6 | 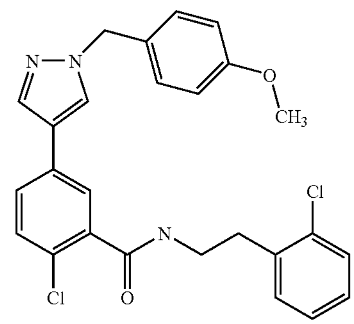 | 2-Chloro-N-[2-(2-chloro-phenyl)-ethyl]-5-[1-(4-methoxy-benzyl)-1H-pyrazol-4-yl]-benzamide | 480.5 |
| 7 | 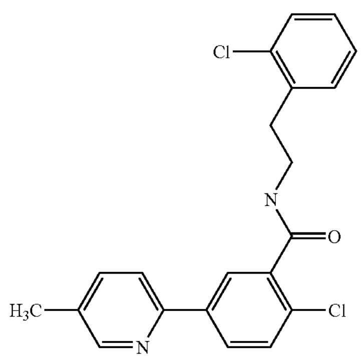 | 2-Chloro-N-[2-(2-chloro-phenyl)-ethyl]-5-(5-methyl-pyridin-2-yl)-benzamide | 385.3 |
| 8 | 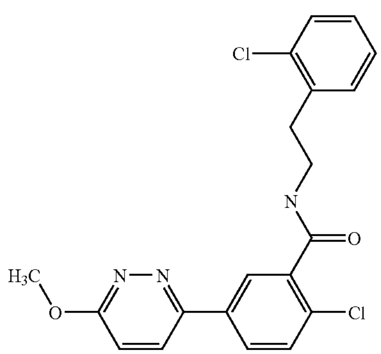 | 2-Chloro-N-[2-(2-chloro-phenyl)-ethyl]-5-(6-methoxy-pyridazin-3-yl)-benzamide | 402.2 |
| 9 | 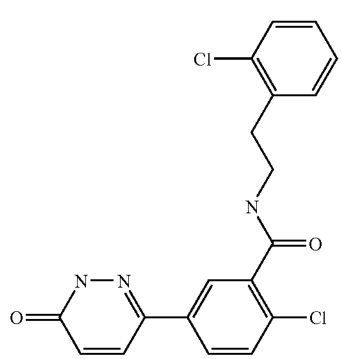 | 2-Chloro-N-[2-(2-chloro-phenyl)-ethyl]-5-(6-oxo-1,6-dihydro-pyridazin-3-yl)-benzamide | 389.4 |

EXAMPLE 10

2-Chloro-N-[2-(2-chloro-phenyl)-ethyl]-5-(1H-pyrazol-4-yl)-benzamide

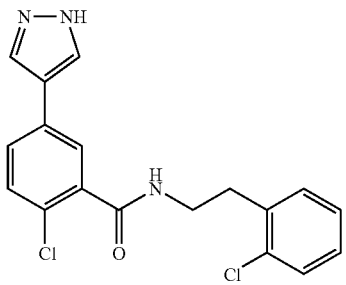

To as solution of 2-chloro-N-[2-(2-chloro-phenyl)-ethyl]-5-[1-(4-methoxy-benzyl)-1H-pyrazol-4-yl]-benzamide (20 mg, 0.042 mmol) in dichloromethane (0.2 mL) was added trifluoroacetic acid (24 mg, 0.21 mmol) and anisole (45 mg, 0.42 mmol). The mixture was stirred at 110° C., for 16 h. A second portion of trifluoroacetic acid (0.2 mL) and anisole (45 μL) was added and the mixture was stirred at 110° C. for a further 6 h. The mixture was concentrated in vacuo to dryness and triturated with hexane to afford the title compound as an orange solid (17 mg). LCMS (m/z) 358.5 M+1.

EXAMPLE 11

2-Chloro-(1-hydroxy-cycloheptylmethyl)-5-(5-methyl-1H-pyrazol-3-yl)-benzamide

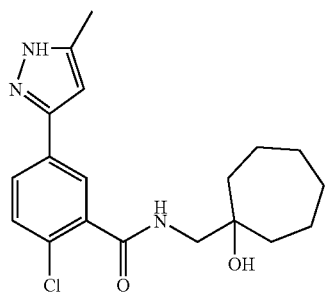

2-Chloro-5-trimethylsilanylethynyl-benzoic acid methyl ester

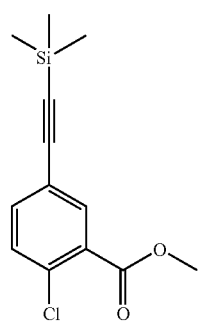

A mixture of 2-chloro-5-iodo-benzoic acid methyl ester (3.5 g, 12 mmol), dichlorobis(triphenylphosphino)palladium (II) (0.04 g, 0.06 mmol), triphenylphosphine (0.06 g, 0.24 mmol), copper iodide (0.05 g, 0.24 mmol), (trimethylsilyl)acetylene (1.9 g, 19.2 mmol) in triethylamine (40 mL) was heated at reflux for 12 h. The mixture was concentrated in vacuo, diluted with ethyl acetate (150 mL) and washed sequentially with 10% aqueous citric acid, water, and brine. The organic solution was dried, filtered and concentrated in vacuo to afford the title compound (3.14 g).

5-Acetyl-2-chloro-benzoic acid methyl ester

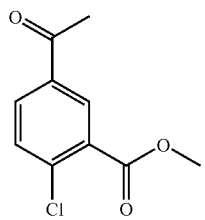

A mixture of 2-chloro-5-trimethylsilanylethynyl-benzoic acid methyl ester (3.2 g, 12 mmol) in formic acid (50 mL) was heated at reflux for 16 h. The mixture was cooled to room temperature and concentrated in vacuo. The residue was diluted with ethyl acetate and washed with saturated aqueous sodium bicarbonate, water and brine. The organic layer was dried, filtered and concentrated in vacuo to afford the title compound (1.4 g).

2-Chloro-5-(5-methyl-1H-pyrazol-3-yl)-benzoic acid methyl ester

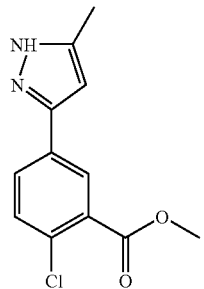

A solution of 5-acetyl-2-chloro-benzoic acid methyl ester (1.58 g, 7.5 mmol) and N,N-dimethylacetamide dimethylacetal in N,N-dimethylformamide and N,N-dimethylacetamide was stirred at 90° C. for 3 h. The mixture was cooled to room temperature and concentrated in vacuo. The residue was diluted with ethanol (18 mL) and tetrahydrofuran (2 mL). Hydrazine hydrate (0.34 mL) was added and the mixture was stirred at room temperature for 16 h. The mixture was concentrated in vacuo. The residue was purified by flash column chromatography (gradient 0-10% methanol-ethyl acetate) to afford the title compound (1.0 g).

55
2-Chloro-5-(5-methyl-1H-pyrazol-3-yl)-benzoic acid

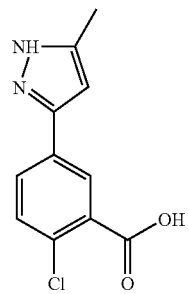

A solution of 2-chloro-5-(5-methyl-1H-pyrazol-3-yl)-benzoic acid methyl ester (4.5 g, 17.0 mmol) in methanol (20.0 mL) was treated with potassium hydroxide (4.52 g, 80.0 mmol). The mixture was stirred at room temperature for 16 h. The mixture was acidified to pH 4.0 with conc. HCl Methanol was removed from the mixture under vacuo. The residue was stirred at rt for 2 h and the solids collected by filtration, washed with water, 2:1 Hexanes/ether and dried to give the title compound (2.2 g)

56
2-Chloro-(1-hydroxy-cycloheptylmethyl)-5-(5-methyl-1H-pyrazol-3-yl)-benzamide

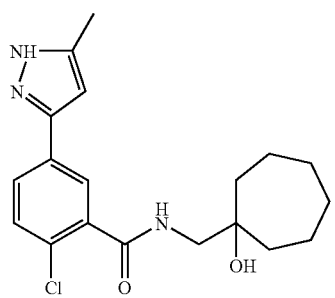

To a solution of 2-chloro-5-(5-methyl-1H-pyrazol-3-yl)-benzoic acid (100 mg, 0.422 mmol) in DMF (10 mL) was added 1-hydroxybenzotriazole (85 mg, 0.63 mmol), polystyrene supported 1-(3-dimethylaminopropyl)-3-ethylcarbodiimide (1.24 g, 1.27 mmol) and 1-aminomethyl-cycloheptanol hydrochloride (113.4 mg, 0.633 mmol). The mixture was stirred at room temperature for 15 minutes, then polystyrene supported N,N-dimethylaminopyridine (0.64 g, 0.93 mmol) was added and the mixture was stirred at room temperature for 16 h. The mixture was filtered through a glass frit, and the residue was washed thoroughly with methanol. The filtrate was concentrated to dryness in vacuo. The residue was purified by reverse phase chromatography to afford the title compound as a white solid (40 mg). LC/MS (M/z): 362.5 (M+1).

The following examples can be made according to the method in Example III:

| EXAMPLES | STRUCTURE | NAME | DATA LCMS M/Z (M + 1) |
|---|---|---|---|
| 12 | 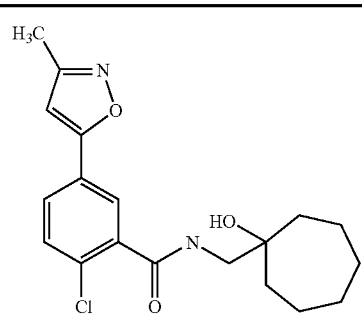 | 2-Chloro-N-(1-hydroxy-cycloheptylmethyl)-5-(3-methyl-isoxazol-5-yl)-benzamide | 363.4 |
| 13 | 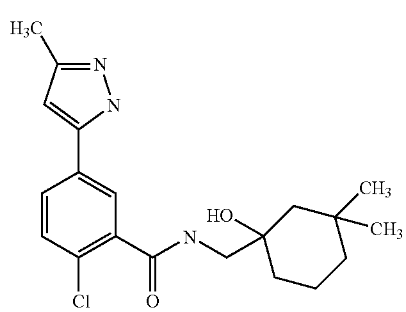 | 2-Chloro-N-(1-hydroxy-3,3-dimethyl-cyclohexylmethyl)-5-(5-methyl-2H-pyrazol-3-yl)-benzamide | 376.6 |

-continued

| EXAMPLES | STRUCTURE | NAME | DATA LCMS M/Z (M + 1) |
|---|---|---|---|
| 14 | 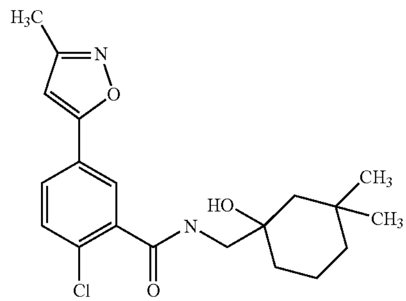 | 2-Chloro-N-(1-hydroxy-3,3-dimethyl-cyclohexylmethyl)-5-(3-methyl-isoxazol-5-yl)-benzamide | 377.5 |
| 15 | 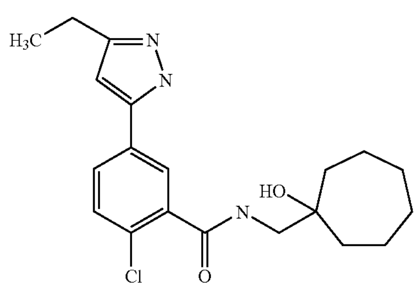 | 2-Chloro-5-(5-ethyl-2H-pyrazol-3-yl)-N-(1-hydroxy-cycloheptylmethyl)-benzamide | 377.5 |
| 16 | 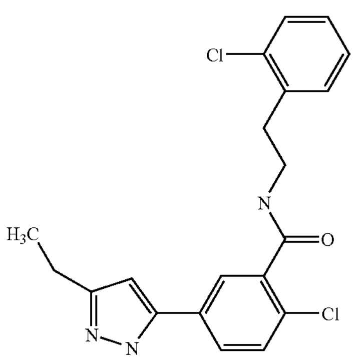 | 2-Chloro-N-[2-(2-chloro-phenyl)-ethyl]-5-(5-ethyl-2H-pyrazol-3-yl)-benzamide | 388.4 |
| 17 | 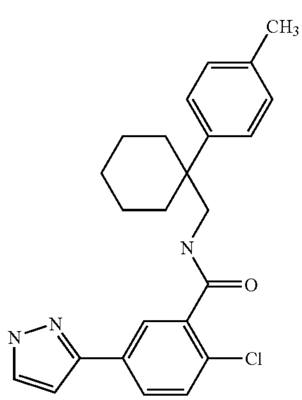 | 2-Chloro-5-(1H-pyrazol-3-yl)-N-(1-p-tolyl-cyclohexylmethyl)-benzamide | 408.6 |

-continued
| EXAMPLES | STRUCTURE | NAME | DATA LCMS M/Z (M + 1) |
|---|---|---|---|
| 18 | 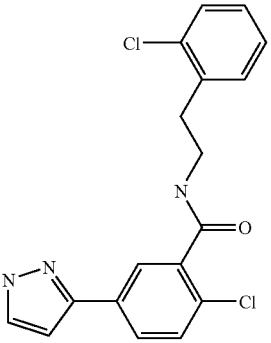 | 2-Chloro-N-[2-(2-chloro-phenyl)-ethyl]-5-(1H-pyrazol-3-yl)-benzamide | 360.5 |
| 19 | 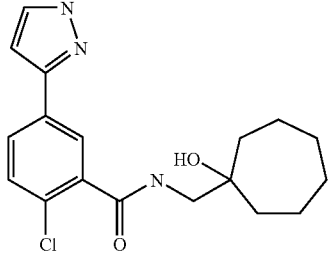 | 2-Chloro-N-(1-hydroxy-cycloheptylmethyl)-5-(1H-pyrazol-3-yl)-benzamide | 348.2 |
| 20 | 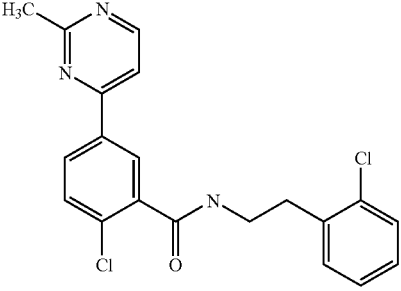 | 2-Chloro-N-[2-(2-chloro-phenyl)-ethyl]-5-(2-methyl-pyrimidin-4-yl)-benzamide | 389.3 |

| EXAMPLES | STRUCTURE | NAME | DATA LCMS M/Z (M + 1) |
|---|---|---|---|
| 21 | 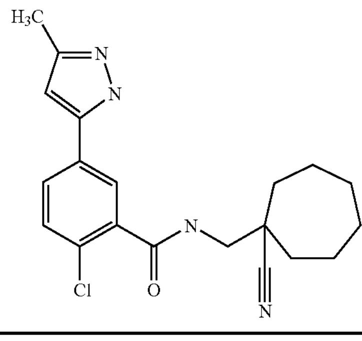 | 2-Chloro-N-(1-cyano-cycloheptylmethyl)-5-(5-methyl-2H-pyrazol-3-yl)-benzamide | 371.3 |

EXAMPLE 22

2-Chloro-5-(5-cyclopropyl-1H-pyrazol-3-yl)-benzoic acid ethyl ester

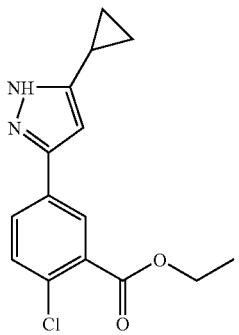

To a solution of 5-acetyl-2-chloro-benzoic acid ethyl ester (0.45 g, 2 mmol) in toluene (10 mL) at 0° C. was added potassium tert-butoxide (2.0 mL, 2 mmol, 1M THF). The mixture was stirred at room temperature for 10 minutes, then cyclopropanecarbonyl chloride (2.0 mL, 2 mmol, 1M toluene) was added. The mixture was stirred at room temperature for 2 h. Polymer bound sulfonic acid (3 eq) was added and the mixture was stirred at room temperature for 10 minutes, filtered, and the filtrate concentrated in vacuo. The residue was dissolved in ethanol (10 mL) and stirred with hydrazine (0.15 mL) at room temperature for 12 h. The mixture was concentrated in vacuo, stirred with silica bound sulfonic acid for 10 minutes, filtered, washed with methanol and eluted with methanolic ammonia (1.0 M). The crude residue was purified by flash column chromatography (hexane-ethyl acetate gradient) to afford the title compound (0.05 g).

2-Chloro-5-(5-cyclopropyl-1H-pyrazol-3-yl)-benzoic acid

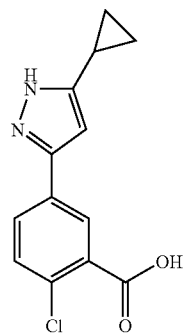

To a solution of 2-chloro-5-(5-cyclopropyl-1H-pyrazol-3-yl)-benzoic acid ethyl ester (0.05 g, 0.17 mmol) in methanol (4 mL) was added KOH (0.12 g). The mixture was shaken at room temperature for 16 h. The mixture was acidified with 10% aqueous citric acid and extracted with ethyl acetate. The combined organic layers were washed with water and brine, and concentrated in vacuo to afford the title compound (0.06 g). 2-Chloro-5-(5-cyclopropyl-1H-pyrazol-3-yl)-N-(1-hydroxy-cycloheptylmethyl)-benzamide

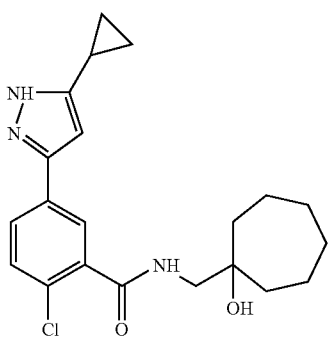

A mixture of 2-chloro-5-(5-cyclopropyl-1H-pyrazol-3-yl)-benzoic acid (0.06 g, 0.23 mmol), 1-aminomethyl-cycloheptanol ((0.082 g, 0.46 mmol), polystyrene supported carbonyldiimidazole (0.37 g, 0.46 mmol), polystyrene supported dimethylaminopyridine (0.32 g, 0.46 mmol) and 1-hydroxybenztriazole (0.06 g, 0.46 mmol) in N,N-dimethylformamide (3 mL) was shaken at room temperature for 16 h. MP-carbonate was added (0.5 g) and the resulting mixture was shaken at room temperature for 2 h. The mixture was filtered and the filtrate was concentrated in vacuo. the residue was purified by reverse phase chromatography to afford the title compound (0.02 g). LCMS (m/z) 388.4 M+1.

The following examples can be made according to the method in Example 22:

| EXAMPLES | STRUCTURE | NAME | DATA LCMS M/Z (M + 1) |
|---|---|---|---|
| 23 | 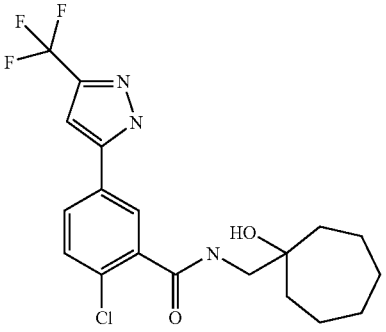 | 2-Chloro-N-(1-hydroxy-cycloheptylmethyl)-5-(5-trifluoromethyl-1H-pyrazol-3-yl)-benzamide | 416.5 |
| 24 | 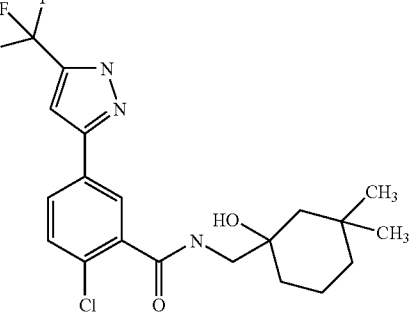 | 2-Chloro-N-(1-hydroxy-3,3-dimethyl-cyclohexylmethyl)-5-(5-trifluoromethyl-1H-pyrazol-3-yl)-benzamide | 430.6 |

EXAMPLE 25

2-Chloro-N-(1-hydroxy-cycloheptylmethyl)-5-[1-(2-hydroxy-ethyl)-5-methyl-1H-pyrazol-3-yl]-benzamide

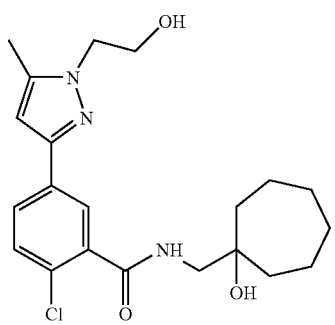

A mixture of 2-chloro-N-(1-hydroxy-cycloheptylmethyl)-5-(5-methyl-1H-pyrazol-3-yl)-benzamide (5.0 g, 13.8 mmol) and cesium carbonate (9.0 g, 27.7 mmol) in dimethylsulfoxide (50 mL) was stirred at room temperature for 10 minutes. Bromoethanol (1.9 g, 15.2 mmol) was added and the resulting mixture was stirred at 80° C. for 12 h. The mixture was cooled to room temperature and filtered. The filtrate was diluted with ethyl acetate (300 mL), washed with water and brine, dried, filtered and concentrated in vacuo. The residue was triturated with dichloromethane-ethyl acetate-diethyl ether (1:1:1, 100 mL) and washed with ethyl acetate to afford the title compound (3.3 g). LCMS (m/z) 406.1 M+1.

The following examples can be made according to the method in Example 25:

| EXAMPLES | STRUCTURE | NAME | DATA LCMS M/Z (M + 1) |
|---|---|---|---|
| 26 | 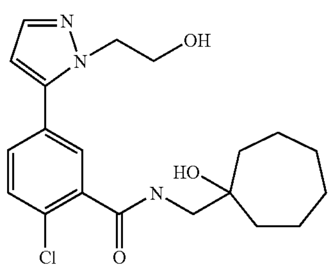 | 2-Chloro-N-(1-hydroxy-cycloheptylmethyl)-5-[2-(2-hydroxy-ethyl)-2H-pyrazol-3-yl]-benzamide | 392.5 |
| 27 | 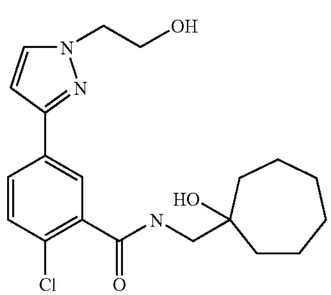 | 2-Chloro-N-(1-hydroxy-cycloheptylmethyl)-5-[1-(2-hydroxy-ethyl)-1H-pyrazol-3-yl]-benzamide | 392.5 |
| 28 | 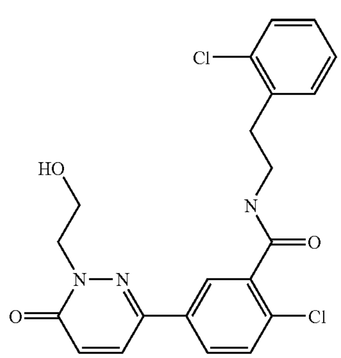 | 2-Chloro-N-[2-(2-chloro-phenyl)-ethyl]-5-[1-(2-hydroxy-ethyl)-6-oxo-1,6-dihydro-pyridazin-3-yl]-benzamide | 432.4 |

-continued

| EXAMPLES | STRUCTURE | NAME | DATA LCMS M/Z (M + 1) |
|---|---|---|---|
| 29 | 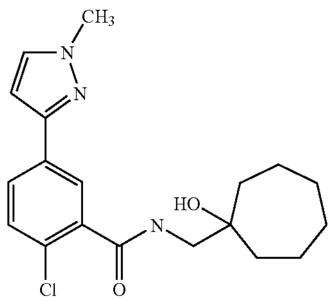 | 2-Chloro-N-(1-hydroxy-cycloheptylmethyl)-5-(1-methyl-1H-pyrazol-3-yl)-benzamide | 362.4 |
| 30 | 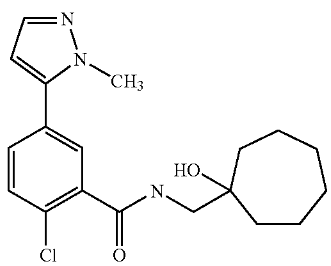 | 2-Chloro-N-(1-hydroxy-cycloheptylmethyl)-5-(2-methyl-2H-pyrazol-3-yl)-benzamide | 362.4 |
| 31 | 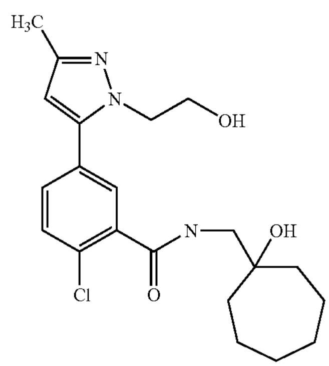 | 2-Chloro-N-(1-hydroxy-cycloheptylmethyl)-5-[2-(2-hydroxy-ethyl)-5-methyl-2H-pyrazol-3-yl]-benzamide | 407.3 |
| 32 | 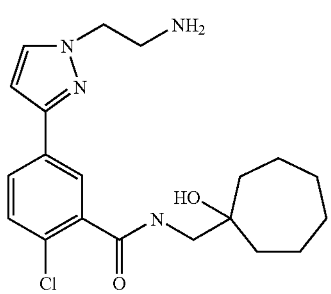 | 5-[1-(2-Amino-ethyl)-1H-pyrazol-3-yl]-2-chloro-N-(1-hydroxy-cycloheptylmethyl)-benzamide | 391.4 |
| 33 | 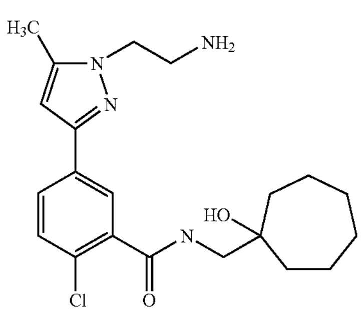 | 5-[1-(2-Amino-ethyl)-5-methyl-1H-pyrazol-3-yl]-2-chloro-N-(1-hydroxy-cycloheptylmethyl)-benzamide | 405.4 |

-continued

| EXAMPLES | STRUCTURE | NAME | DATA LCMS M/Z (M + 1) |
|---|---|---|---|
| 34 | 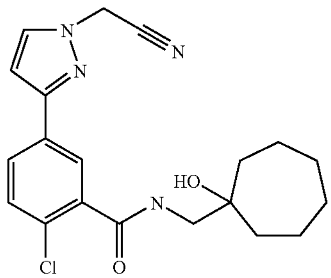 | 2-Chloro-5-(1-cyanomethyl-1H-pyrazol-3-yl)-N-(1-hydroxy-cycloheptylmethyl)-benzamide | 387.5 |
| 35 | 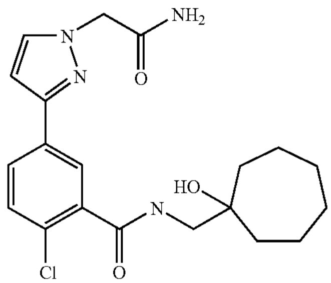 | 5-(1-Carbamoylmethyl-1H-pyrazol-3-yl)-2-chloro-N-(1-hydroxy-cycloheptylmethyl)-benzamide | 405.4 |
| 36 | 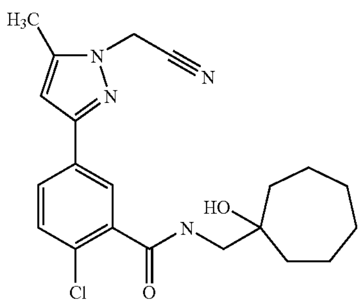 | 2-Chloro-5-(1-cyanomethyl-5-methyl-1H-pyrazol-3-yl)-N-(1-hydroxy-cycloheptylmethyl)-benzamide | 401.5 |
| 37 | 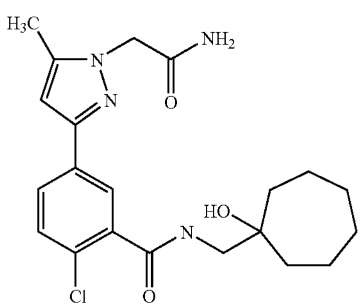 | 5-(1-Carbamoylmethyl-5-methyl-1H-pyrazol-3-yl)-2-chloro-N-(1-hydroxy-cycloheptylmethyl)-benzamide | 419.4 |
| 38 | 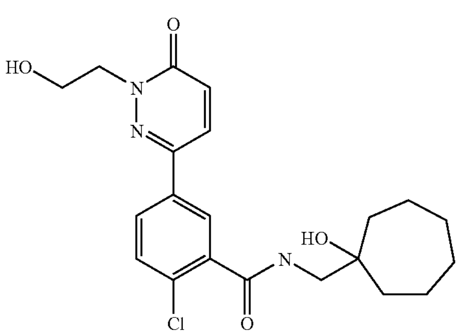 | 2-Chloro-N-(1-hydroxy-cycloheptylmethyl)-5-[1-(2-hydroxy-ethyl)-6-oxo-1,6-dihydro-pyridazin-3-yl]-benzamide | 420.5 |

EXAMPLE 39

2-Chloro-N-(1-hydroxy-cycloheptylmethyl)-5-[1-(2-hydroxy-3-methoxy-propyl)-5-methyl-1H-pyrazol-3-yl]-benzamide

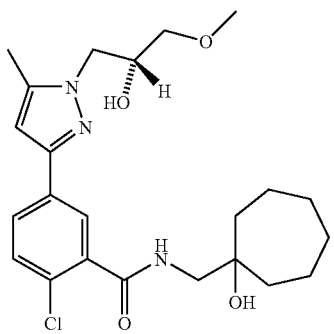

A mixture of 2-chloro-N-(1-hydroxy-cycloheptylmethyl)-5-(5-methyl-1H-pyrazol-3-yl)-benzamide (0.36 g, 1 mmol) and 2-methoxymethyl-oxirane (0.8 mL) was stirred in N,N-dimethylformamide (1.0 mL) at 90° C. for 12 h. The mixture was concentrated in vacuo. The residue was purified by reverse phase chromatography, followed by trituration (1:1:1 diethyl ether-dichloromethane-ethyl acetate) to afford the title compound (0.08 g). LCMS (m/z) 450.1 M+1

The following examples can be made according to the method in Example 39:

| EXAMPLE | STRUCTURE | NAME | DATA LCMS M/Z (M + 1) |
|---|---|---|---|
| 40 | 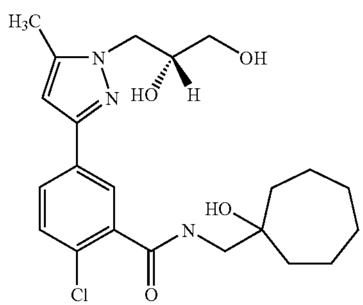 | 2-Chloro-5-[1-(2,3-dihydroxy-propyl)-5-methyl-1H-pyrazol-3-yl]-N-(1-hydroxy-cycloheptylmethyl)-benzamide | 436.2 |
| 41 | 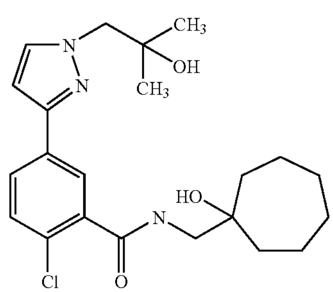 | 2-Chloro-N-(1-hydroxy-cycloheptylmethyl)-5-[1-(2-hydroxy-2-methyl-propyl)-1H-pyrazol-3-yl]-benzamide | 420.6 |
| 42 | 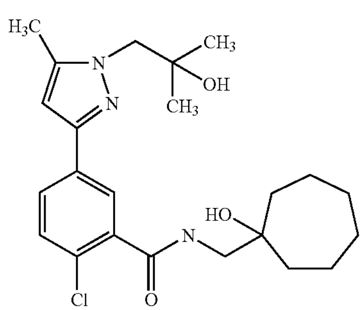 | 2-Chloro-N-(1-hydroxy-cycloheptylmethyl)-5-[1-(2-hydroxy-2-methyl-propyl)-5-methyl-1H-pyrazol-3-yl]-benzamide | 434.4 |

-continued

| EXAMPLE | STRUCTURE | NAME | DATA LCMS M/Z (M + 1) |
|---|---|---|---|
| 43 | 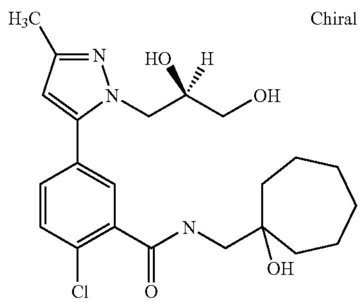 | Chiral 2-Chloro-5-[2-(2,3-dihydroxy-propyl)-5-methyl-2H-pyrazol-3-yl]-N-(1-hydroxy-cycloheptylmethyl)-benzamide | 436.6 |
| 44 | 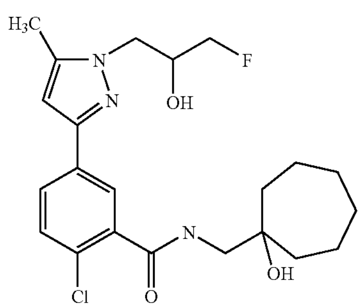 | 5-[1-(3-Amino-2-hydroxy-propyl)-5-methyl-1H-pyrazol-3-yl]-2-chloro-N-(1-hydroxy-cycloheptylmethyl)-benzamide | 435.5 |
| 45 | 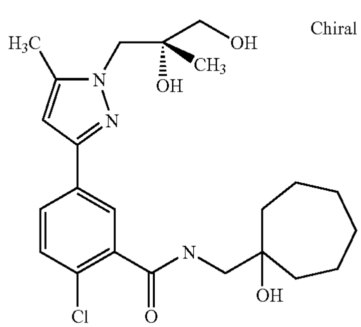 | Chiral 2-Chloro-5-[1-(2,3-dihydroxy-2-methyl-propyl)-5-methyl-1H-pyrazol-3-yl]-N-(1-hydroxy-cycloheptylmethyl)-benzamide | |

EXAMPLE 46

(3-{4-Chloro-3-[(1-hydroxy-cycloheptylmethyl)-carbamoyl]-phenyl}-5-methyl-pyrazol-1-yl)-acetic acid methyl ester

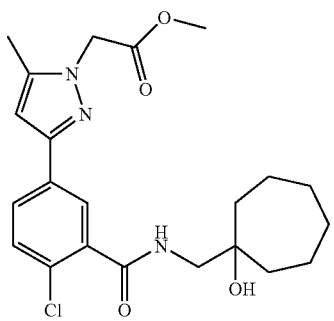

A mixture of 2-chloro-N-(1-hydroxy-cycloheptylmethyl)-5-(5-methyl-1H-pyrazol-3-yl)-benzamide (1.08 g, 3 mmol), 2-tert-butylimino-2-diethylamino-1,3-dimethyl-perhydro-1,2,3-diazaphosphorine on polystyrene (2.0 g, 4.6 mmol) and bromo-acetic acid methyl ester (0.69 g, 4.5 mmol) in N,N-dimethylformamide (10 mL) was stirred at room temperature for 2 h. The mixture was filtered and washed with dichloromethane. The filtrate was concentrated in vacuo. The residue was triturated with ethyl acetate to afford the title compound (1.05 g). (3-{4-Chloro-3-[(1-hydroxy-cycloheptylmethyl)-carbamoyl]-phenyl}-5-methyl-pyrazol-1-yl)-acetic acid.

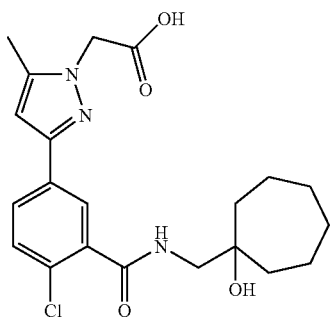

A mixture of (3-{4-chloro-3-[(1-hydroxy-cycloheptylmethyl)-carbamoyl]-phenyl}-5-methyl-pyrazol-1-yl)-acetic acid methyl ester (1.63 g, 3.76 mmol) and potassium hydroxide (1.12 g, 20 mmol) in methanol (25 mL) and water (5 mL) was stirred at room temperature for 6 h. The mixture was acidified to pH 6 with 10% aqueous citric acid and concentrated in vacuo. 1M HCl was added until the mixture reached pH 4. The resulting solids were collected by filtration and washed sequentially with water, hexanes and diethyl ether to afford the title compound (1.1 g).

2-Chloro-N-(1-hydroxy-cycloheptylmethyl)-5-[5-methyl-1-(2-oxo-2-pyrrolidin-1-yl-ethyl)-1H-pyrazol-3-yl]-benzamide

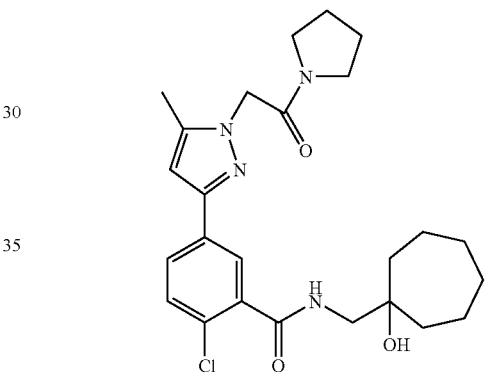

To a solution of (3-{4-chloro-3-[(1-hydroxy-cycloheptylmethyl)-carbamoyl]-phenyl}-5-methyl-pyrazol-1-yl)-acetic acid (41.9 mg, 0.1 mmol) in N,N-dimethylformamide (1 mL) was added a solution of 1-hydroxybenzotriazole (20.25 mg, 0.15 mmol) in N,N-dimethylformamide (0.5 mL) and carbonyldiimidazole on polystyrene (294 mg, 0.3 mmol). The mixture was shaken at room temperature for 10 minutes. Pyrrolidine (10.65 mg, 0.15 mmol) was added as a solution in N,N-dimethylformamide (1.5 mL). Polystyrene supported dimethylaminopyridine (152 mg, 0.22 mmol) was added and the mixture was shaken at room temperature for 16 h. MP-carbonate resin (139 mg, 0.4 mmol) was added and the mixture was shaken at room temperature for 3 h. The mixture was filtered, washed with methanol and concentrated in vacuo. The residue was purified by reverse phase chromatography to afford the title compound (22 mg). LCMS (m/z) 473.4 M+1.

The following examples can be made according to the method in Example 47:

| EXAMPLES | STRUCTURE | NAME | DATA LCMS M/Z (M + 1) |
|---|---|---|---|
| 47 | 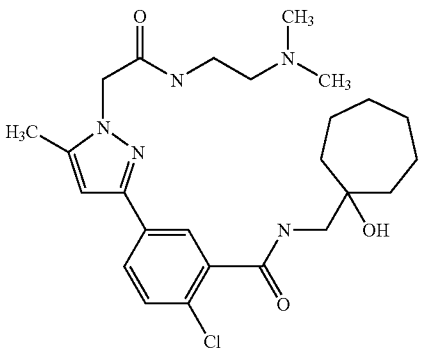 | 2-Chloro-5-{1-[(2-dimethylamino-ethylcarbamoyl)-methyl]-5-methyl-1H-pyrazol-3-yl}-N-(1-hydroxy-cycloheptylmethyl)-benzamide | 490.4 |
| 48 | 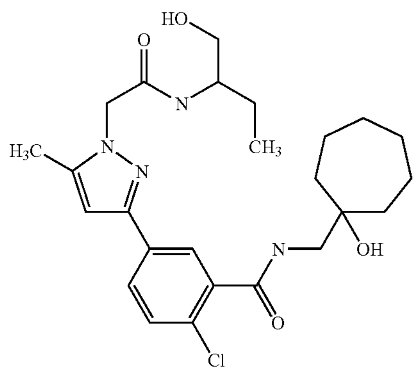 | 2-Chloro-N-(1-hydroxy-cycloheptylmethyl)-5-{1-[(1-hydroxymethyl-propylcarbamoyl)-methyl]-5-methyl-1H-pyrazol-3-yl}-benzamide | 491.4 |
| 49 | 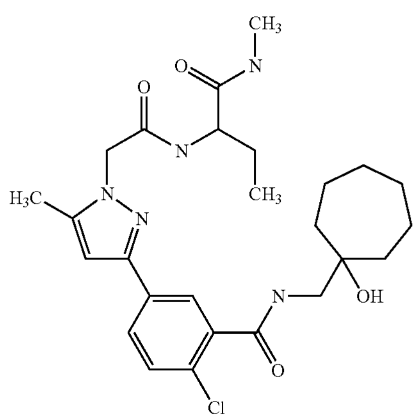 | 2-Chloro-N-(1-hydroxy-cycloheptylmethyl)-5-{5-methyl-1-[(methylcarbamoylmethyl-carbamoyl)-methyl]-1H-pyrazol-3-yl}-benzamide | 490.4 |
| 50 | 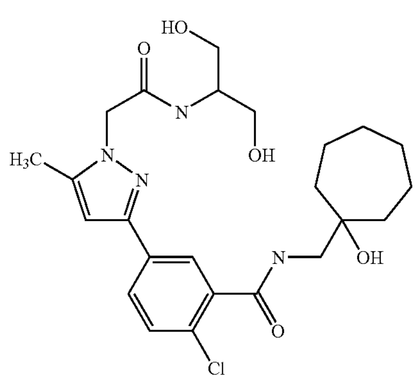 | 2-Chloro-N-(1-hydroxy-cycloheptylmethyl)-5-{1-[(2-hydroxy-1-hydroxymethyl-ethylcarbamoyl)-methyl]-5-methyl-1H-pyrazol-3-yl}-benzamide | 493.4 |

| EXAMPLES | STRUCTURE | NAME | DATA LCMS M/Z (M + 1) |
|---|---|---|---|
| 51 | 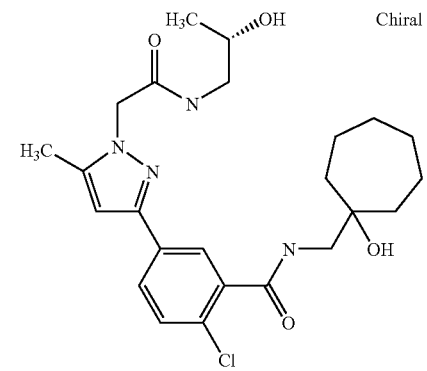 Chiral | 2-Chloro-N-(1-hydroxy-cycloheptylmethyl)-5-{1-[(2-hydroxy-propylcarbamoyl)-methyl]-5-methyl-1H-pyrazol-3-yl}-benzamide | 477.4 |
| 52 | 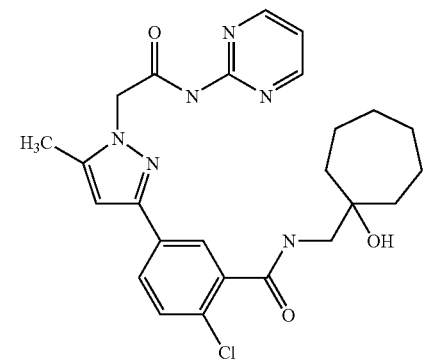 | 2-Chloro-N-(1-hydroxy-cycloheptylmethyl)-5-[5-methyl-1-(pyrimidin-2-ylcarbamoylmethyl)-1H-pyrazol-3-yl]-benzamide | 497.5 |

| EXAMPLES | STRUCTURE | NAME | DATA LCMS M/Z (M + 1) |
|---|---|---|---|
| 53 | (structure, Chiral) | 2-Chloro-5-{1-[2-(3,4-dihydroxy-pyrrolidin-1-yl)-2-oxo-ethyl]-5-methyl-1H-pyrazol-3-yl}-N-(1-hydroxy-cycloheptylmethyl)-benzamide | 505.3 |

EXAMPLE 54

2-Chloro-N-(1-hydroxy-cycloheptylmethyl)-5-(5-methyl-1-oxiranylmethyl-1H-pyrazol-3-yl)-benzamide A mixture of 2-chloro-N-(1-hydroxy-cycloheptylmethyl)-5-(5-methyl-1H-pyrazol-3-yl)-benzamide (3.95 g, 11 mmol), 2-tert-butylimino-2-diethylamino-1,3-dimethyl-perhydro-1,2,3-diazaphosphorine on polystyrene (10.0 g, 23 mmol) in acetonitrile (60 mL) and N,N-dimethylformamide (20 mL) was stirred at room temperature for 10 minutes. 2R-(−)-glycidyl 3-nitrobenzenesulfonate (3.0 g, 12.5 mmol) was added and the resulting mixture was stirred at 80° C. for 8 h. The mixture was filtered and concentrated in vacuo. the residue was purified by flash column chromatography (gradient dichloromethane-ethyl acetate-methanol) to afford the title compound (2.5 g).

5-[1-(3-Amino-2-hydroxy-propyl)-5-methyl-1H-pyrazol-3-yl]-2-chloro-N-(1-hydroxy-cycloheptylmethyl)-benzamide A mixture of 2-chloro-N-(1-hydroxy-cycloheptylmethyl)-5-(5-methyl-1-oxiranylmethyl-1H-pyrazol-3-yl)-benzamide (0.4 g, 0.96 mmol) in methanolic ammonia (20 mL, 7.0 N) was heated to 67° C. in a sealed tube for 16 h. The mixture was concentrated in vacuo, and the residue was triturated with diethyl ether-ethyl acetate to afford the title compound (0.12 g). LCMS (m/z) 435.3 M+1.

5-[1-(3-Amino-2-hydroxy-propyl)-5-methyl-1H-pyrazol-3-yl]-2-chloro-N-(1-hydroxy-cycloheptylmethyl)-benzamide Hydrochloride To a solution of 5-[1-(3-Amino-2-hydroxy-propyl)-5-methyl-1H-pyrazol-3-yl]-2-chloro-N-(1-hydroxy-cycloheptyl-methyl)-benzamide (1.05 g, 2.41 mmol) in dichloromethane (10.0 mL) was added 2.0 N Hydrochloric acid in diethylether (4.0 mL, 8.0 mmol). The mixture was diluted with ether (50 mL) and stirred for 15 min. The precipitated solids were collected by filtration, washed with ether and dried to give title compound (1.0 g): LCMS (m/z) 435.3 M+1.

The following examples can be made according to the method in Example 55:

| EXAMPLE | STRUCTURE | NAME | DATA LCMS M/Z |
|---|---|---|---|
| 55 | Chiral | 5-[2-(3-Amino-2-hydroxy-propyl)-5-methyl-2H-pyrazol-3-yl]-2-chloro-N-(1-hydroxy-cycloheptylmethyl)-benzamide | 435.5 |

EXAMPLE 56

2-Chloro-5-(2H-[1,2,3]triazol-4-yl)-benzoic acid methyl ester

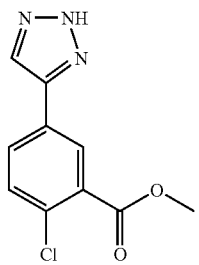

A mixture of 2-chloro-5-ethynyl-benzoic acid methyl ester (0.18 g, 0.92 mmol) and trimethylsilyl azide (0.16 g, 1.39 mmol) in n-butanol was heated to reflux for 16 h. A second portion of trimethylsilyl azide (0.16 g, 1.39 mmol) was added and the mixture was refluxed for a further 16 h. A third portion of trimethylsilyl azide (0.16 g, 1.39 mmol) was added and the mixture was refluxed for a further 16 h. Silica gel was added and the mixture was concentrated in vacuo. The residue was purified by flash column chromatography (2:1 hexanes-ethyl acetate) to afford the title compound (0.095 g).

2-Chloro-5-(2H-[1,2,3]triazol-4-yl)-benzoic acid

To a solution of 2-chloro-5-(2H-[1,2,3]triazol-4-yl)-benzoic acid methyl ester (0.095 g, 0.4 mmol) in methanol (2 mL) was added potassium hydroxide (0.25 g). The mixture was shaken at room temperature for 12 h. The mixture was diluted with methanol and acidified with HCl (2 mL, 6M). The mixture was concentrated in vacuo, diluted with water and sonicated. The solids were collected by filtration and washed with hexanes to afford the title compound (0.075 g).

2-Chloro-N-(1-hydroxy-cycloheptylmethyl)-5-(2H-[1,2,3]triazol-4-yl)-benzamide

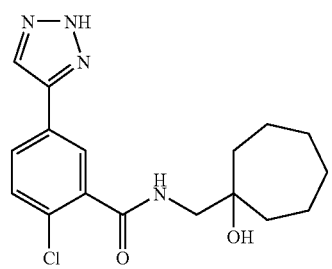

To a solution of 2-chloro-5-(2H-[1,2,3]triazol-4-yl)-benzoic acid (0.03 g, 0.136 mmol) in DMF (1.0 mL) was added 1-hydroxybenzotriazole (28 mg, 0.204 mmol), polystyrene supported 1-(3-dimethylaminopropyl)-3-ethylcarbodiimide (0.4 g, 0.4 mmol) and 1-aminomethyl-cycloheptanol hydrochloride (0.036 g, 0.204 mmol). The mixture was stirred at room temperature for 10 minutes, then polystyrene supported N,N-dimethylaminopyridine (0.2 g, 0.29 mmol) was added and the mixture was shaken at room temperature for 16 h. MP-carbonate was added (200 mg) and the mixture was shaken at room temperature for 3 h. The mixture was filtered and washed with methanol. the filtrate was concentrated in vacuo and purified by reverse phase chromatography to afford the title compound (22 mg). LCMS (m/z) 349.3 M+1.

EXAMPLE 57

2-Chloro-N-(1-hydroxy-cycloheptylmethyl)-5-(1H-imidazol-4-yl)-benzamide

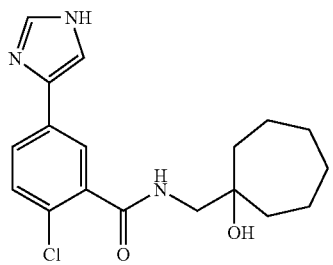

A solution of 2-chloro-5-formyl-N-(1-hydroxy-cycloheptylmethyl)-benzamide (50 mg, 0.16 mmol) and ammonium hydroxide (0.5 mL, 0.44 mmol) in THF (5 mL) was stirred at room temperature for 6 h. p-Toluenesufonylmethylisocyanate (21 mg, 0.11 mmol) and piperazine (14 mg, 0.16 mmol) were added and the mixture was stirred at room temperature for 5 d. The mixture was diluted with ethyl acetate and water. The organic layer was washed with brine, dried over sodium sulfate, filtered and concentrated in vacuo. The residue was dissolved in HCl (20 mL, 1M) and washed with ethyl acetate. The aqueous layer was saponified to pH 12 with sodium hydroxide (6M) and extracted with ethyl acetate. The combined organic layers were washed with brine, dried over sodium sulfate, filtered and concentrated in vacuo to afford the title compound as a white solid (12 mg).

2-Chloro-5-[1-(3-fluoro-2-hydroxy-propyl)-1H-imidazol-4-yl]-N-(1-hydroxy-cycloheptylmethyl)-benzamide

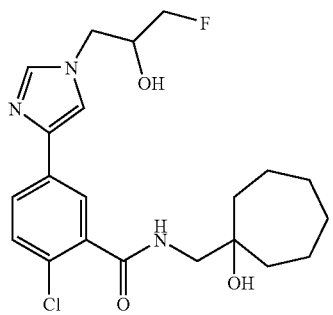

A solution of 2-chloro-N-(1-hydroxy-cycloheptylmethyl)-5-(1H-imidazol-4-yl)-benzamide (5 mg, 0.014 mmol) and 2-fluoromethyl-oxirane (0.06 mL, 0.086 mmol) in N,N-dimethylformamide (0.2 mL) was heated at 65° C. in a sealed tube for 20 h. The mixture was diluted with ethyl acetate and washed with water, and brine, dried over sodium sulfate, filtered and concentrated in vacuo to afford the title compound (5.2 mg).

EXAMPLE 58

2-Chloro-N-(1-hydroxy-cycloheptylmethyl)-5-(hydroxyimino-methyl)-benzamide

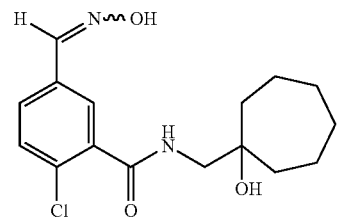

A solution of 2-chloro-5-formyl-N-(1-hydroxy-cycloheptylmethyl)-benzamide (290 mg, 0.94 mmol), hydroxylamine hydrochloride (78 mg, 1.13 mmol) and sodium acetate (223 mg, 2.72 mmol) in methanol (5 mL) and water (5 mL) was stirred at room temperature for 3 h. The mixture was diluted with water and extracted with ethyl acetate. The combined organic layers were washed with water, and brine, dried over sodium sulfate, filtered and adsorbed onto silica gel. The residue was purified by chromatography (1:1 ethyl acetate-hexane) to afford the title compound (140 mg).

2-Chloro-N-(1-hydroxy-cycloheptylmethyl)-5-[5-(2-hydroxy-ethyl)-isoxazol-3-yl]-benzamide

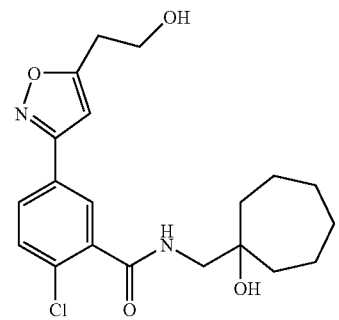

A mixture of 2-chloro-N-(1-hydroxy-cycloheptylmethyl)-5-(hydroxyimino-methyl)-benzamide (50 mg, 0.15 mmol), but-3-yn-1-ol (27 mg, 0.38 mmol), sodium hypochlorite (1 mL, 4%) and triethylamine (2 drops) in dichloromethane (2 mL) was stirred at room temperature for 5 d. The mixture was diluted with water and extracted with ethyl acetate. The combined organic layers were washed with water, and brine, dried over sodium sulfate, filtered and adsorbed onto silica gel. The residue was purified by flash column chromatography (65% ethyl acetate-hexanes) to afford the title compound (13 mg).

EXAMPLE 59

5-(2-Bromo-acetyl)-2-chloro-benzoic acid methyl ester

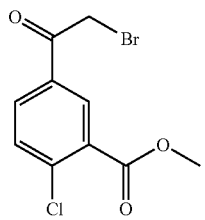

To a solution of 5-acetyl-2-chloro-benzoic acid methyl ester (100 mg, 0.47 mmol) in glacial acetic acid (5 mL) was added bromine (0.05 mL, 0.94 mmol). The mixture was stirred at room temperature for 2 h. Hydrobromic acid-acetic acid (2 drops, 30%) was added and the mixture was stirred for 10 minutes. The mixture was concentrated in vacuo to afford the title compound (140 mg).

2-Chloro-5-(2-methyl-thiazol-4-yl)-benzoic acid methyl ester

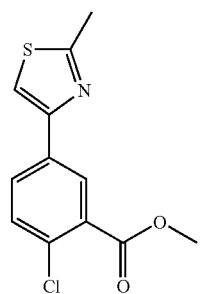

A mixture of 5-(2-bromo-acetyl)-2-chloro-benzoic acid methyl ester (25 mg, 0.09 mmol) and thioacetamide (6.5 mg, 0.08 mmol) in ethanol (2 mL) and stirred at 50° C. for 15 minutes. The mixture was cooled to room temperature and concentrated in vacuo. The residue was dissolved in ethyl acetate, washed with water, and brine, dried over sodium sulfate, filtered and concentrated in vacuo to afford the title compound (10 mg).

2-Chloro-5-(2-methyl-thiazol-4-yl)-benzoic acid

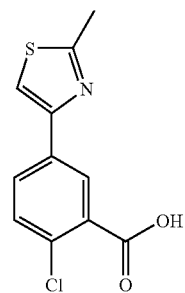

A mixture of 2-chloro-5-(2-methyl-thiazol-4-yl)-benzoic acid methyl ester (10 mg, 0.04 mmol) and sodium hydroxide (80 µL, 1M aqueous, 0.08 mmol) in tert-butanol (1 mL) was stirred at room temperature for 3 d. The mixture was concentrated to dryness in vacuo, dissolved in water (5 mL), acidified to pH 6 (1M HCl) and extracted with ethyl acetate. The combined organic layers were washed with water, and brine, dried over sodium sulfate, filtered and concentrated in vacuo to afford the title compound (7 mg).

2-Chloro-N-(1-hydroxy-cycloheptylmethyl)-5-(2-methyl-thiazol-4-yl)-benzamide

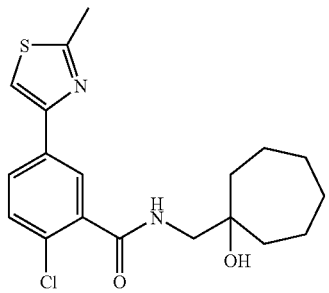

A mixture of 2-chloro-5-(2-methyl-thiazol-4-yl)-benzoic acid (7 mg, 0.027 mmol), 1-aminomethyl-cycloheptanol (6 mg, 0.03 mmol), 1-hydroxybenzotriazole (5 mg, 0.03 mmol), 1-(3-dimethylaminopropyl)-3-ethylcarbodiimide hydrochloride (6 mg, 0.03 mmol) and triethylamine (5 µL, 0.03 mmol) in N,N-dimethylformamide (0.5 mL) was stirred at room temperature for 16 h. The mixture was diluted with ethyl acetate and washed with 5% citric acid, water, then brine. The organic layer was dried over sodium sulfate, filtered, and concentrated in vacuo. The residue was purified by column chromatography (1:1 ethyl acetate-hexanes) to afford the title compound (3.4 mg).

EXAMPLE 60

Compounds of Examples 1-59 were tested for antagonist activity at the P2X$_7$ receptor using the cytokine IL-1β as the readout. Blood was collected from normal volunteers in the presence of heparin, and was fractionated using lymphocyte separation medium obtained from Organon Technica (Westchester, Pa.). The region of the resulting gradient containing banded mononuclear cells was harvested, diluted with 10 ml of Maintenance Medium (RPMI 1640, 5% FBS, 25 mM Hepes, pH 7.2, 1% penicillin/streptomycin), and the mononuclear cells were collected by centrifugation. The resulting cell pellet was suspended in 10 ml of Maintenance Medium and a cell count was performed. Approximately, $2 \times 10^5$ mononuclear cells were seeded into each well of 96-well plates in a total volume of 0.1 ml. Monocytes were allowed to adhere for 2 hours, after which the supernatants were discarded and the attached cells were rinsed twice and then incubated in Maintenance Medium overnight at 37° C. in a 5% $CO_2$ environment.

The cultured monocytes were activated with 10 ng/ml LPS (*E. coli* serotype 055:B5; Sigma Chemicals, St. Louis, Mo.). Following a 2-hour incubation, the activation medium was removed, the cells were rinsed twice with 0.1 ml of Chase Medium (RPMI 1640, 1% FBS, 20 mM Hepes, 5 mM NaHCO$_3$, pH 6.9), and then 0.1 ml of Chase Medium containing a compound of Example 1-59 was added and the plate was incubated for 30 minutes; each compound of Example 1-59 was evaluated in triplicate wells. ATP then was introduced (from a 100 mM stock solution, pH 7) to achieve a final concentration of 2 mM and the plate was incubated at 37° C. for an additional 3 hours. Media were harvested and clarified by centrifugation, and their IL-1β content was determined by ELISA (R&D Systems; Minneapolis, Minn.). The ability of a compound of Example 1-59 to inhibit 50% of the stimulation of the release of IL-1β from monocytes by ATP (i.e., the "IC$_{50}$") is reported in Table 1:

TABLE 1

| Example | IC$_{50}$ (μM) |
|---|---|
| 1 | 0.029 |
| 2 | 0.011 |
| 3 | 0.117 |
| 4 | 0.28 |
| 5 | 0.93 |
| 6 | 1.4 |
| 7 | 1.66 |
| 8 | 0.525 |
| 9 | 1 |
| 10 | 0.8 |
| 11 | 0.00867 |
| 12 | 0.24 |
| 13 | 0.008 |
| 14 | 0.081 |
| 15 | 0.023 |
| 16 | 0.37 |
| 17 | 0.018 |
| 18 | 0.545 |
| 19 | 0.18 |
| 20 | 1 |
| 21 | 0.046 |
| 22 | 0.05 |
| 23 | 0.2 |
| 24 | 1 |
| 25 | 0.004 |
| 26 | 0.373 |
| 27 | 0.031 |
| 28 | 1 |
| 29 | 0.242 |
| 30 | 1 |
| 31 | 0.07 |
| 32 | 0.038 |
| 33 | 0.011 |
| 34 | 0.193 |
| 35 | 0.121 |
| 36 | 0.051 |
| 37 | 0.018 |
| 38 | 0.245 |
| 39 | 0.008 |
| 40 | 0.008 |
| 41 | 0.030 |
| 42 | 0.008 |
| 43 | 0.13 |
| 44 | 0.0025 |
| 45 | 0.006 |
| 46 | 0.022 |
| 47 | 0.0035 |
| 48 | 0.0105 |
| 49 | 0.005 |
| 50 | 0.005 |
| 51 | 0.005 |
| 52 | 0.008 |
| 53 | 0.0155 |
| 54 | 0.005 |
| 55 | 0.365 |

TABLE 1-continued

| Example | IC$_{50}$ (μM) |
|---|---|
| 56 | 0.48 |
| 57 | >1 |
| 58 | 0.43 |
| 59 | 0.28 |

The invention claimed is:

1. A compound of the formula

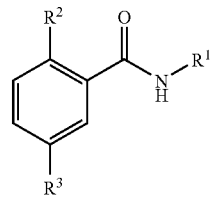

I wherein R$^1$ is methyl or ethyl optionally substituted with one or two groups independently selected from hydroxyl, (C$_6$-C$_7$)cycloalkyl and phenyl; wherein said (C$_6$-C$_7$)cycloalkyl and phenyl may be optionally substituted by one to three radicals independently selected from hydroxyl, halo, methyl and phenyl;

R$^2$ is halo;

R$^3$ is an optionally substituted carbon linked 6-membered heteroaryl or heterocyclyl group selected from the group of:

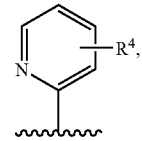

(a)

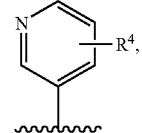

(b)

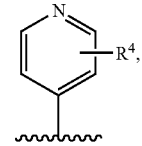

(c)

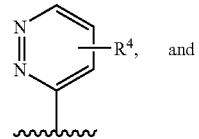

(d)

and

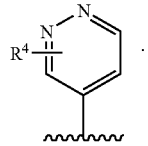

(e)

wherein R$^4$ is independently selected from the group consisting of hydrogen, methyl and (C$_1$-C$_6$)alkoxy;

wherein the molecular weight of said compound of formula I is less than 700 AMU; or a pharmaceutically acceptable salt thereof.

2. A compound of claim 1 selected from the group of:

2-Chloro-N-[2-(2-chloro-phenyl)-ethyl]-5-(6-oxo-1,6-dihydro-pyrazin-3-yl)benzamide;

2-Chloro-N-(1-hydroxy-cycloheptylmethyl)-5-(6-oxo-1,6-dihydro-pyridazin-3-yl)benzamide;

2-Chloro-N-[2-(2-chloro-phenyl)-ethyl]-5-(5-methyl-pyridin-2-yl)-benzamide;

2-Chloro-5-(6-methyl-pyridin-3-yl)-N-(1-p-tolyl-cyclohexylmethyl)-benzamide;

2-Chloro-N-(1-hydroxy-3,3-dimethyl-cyclohexylmethyl)-5-(5-methyl-pyridin-2-yl)-benzamide;

2-Chloro-N-(1hydroxy-cycloheptylmethyl)-5-(5-methyl-pyridin-2-yl)-benzamide;

2-Chloro-N-(1hydroxy cycloheptylmethyl)5(6methoxy-pyridazin-3-yl)-benzamide;

2-Chloro-N-[2-(2-chloro-phenyl)-ethyl]-5-(6-methoxy-pyridazin-3-yl)-benzamide;

2-Chloro-N-[2-(2-chloro-phenyl)-ethyl]-5-(2-methyl-pyrimidin-4-yl)-benzamide;

2-Chloro-N-[2-(2-chloro-phenyl)-ethyl]-5-[1-(2-hydroxy-ethyl)-6-oxo-1,6-dihydro-pyridazin-3-yl]-benzamide; and 2-Chloro-N-(1-hydroxy-cycloheptylmethyl)-5-[1-(2-hydroxy-ethyl)-6-oxo-1,6-dihydro-pyridazin-3-yl]-benzamide; or a pharmaceutically acceptable salt thereof.

3. A pharmaceutical composition comprising a therapeutically effective amount of a compound according to claim 1 or a pharmaceutically acceptable salt thereof, and a pharmaceutically acceptable carrier or diluent.

* * * * *